US009757445B2

(12) United States Patent
Lawrence et al.

(10) Patent No.: US 9,757,445 B2
(45) Date of Patent: Sep. 12, 2017

(54) **ATTENUATED *PASTEURELLA MULTOCIDA* VACCINES AND METHODS OF MAKING AND USE THEREOF**

(71) Applicant: MERIAL LIMITED, Duluth, GA (US)

(72) Inventors: Paulraj Kirubakaran Lawrence, Worthington, MN (US); Russell F. Bey, Arden Hills, MN (US)

(73) Assignee: MERIAL INC., Duluth, GA (US)

( * ) Notice: Subject to any disclaimer, the term of this patent is extended or adjusted under 35 U.S.C. 154(b) by 0 days.

(21) Appl. No.: 14/528,305

(22) Filed: Oct. 30, 2014

(65) Prior Publication Data

US 2015/0125487 A1    May 7, 2015

Related U.S. Application Data

(60) Provisional application No. 61/898,497, filed on Nov. 1, 2013.

(51) Int. Cl.

| *A61K 39/295* | (2006.01) |
| *A61K 39/102* | (2006.01) |
| *A61K 39/12* | (2006.01) |
| *A61K 39/135* | (2006.01) |
| *C12N 7/00* | (2006.01) |
| *A61K 39/00* | (2006.01) |

(52) U.S. Cl.
CPC ............ *A61K 39/102* (2013.01); *A61K 39/12* (2013.01); *A61K 39/135* (2013.01); *C12N 7/00* (2013.01); *A61K 2039/522* (2013.01); *A61K 2039/552* (2013.01); *A61K 2039/55588* (2013.01); *A61K 2039/55594* (2013.01); *A61K 2039/70* (2013.01); *C12N 2760/00034* (2013.01); *C12N 2770/32134* (2013.01)

(58) Field of Classification Search
None
See application file for complete search history.

(56) References Cited

U.S. PATENT DOCUMENTS

| 4,293,545 A | 10/1981 | Kucera |
| 4,388,299 A | 6/1983 | Kucera |
| 4,559,306 A | 12/1985 | Kucera |
| 4,999,191 A | 3/1991 | Glisson et al. |
| 5,587,305 A | 12/1996 | Briggs et al. |
| 5,840,556 A | 11/1998 | Briggs et al. |
| 6,013,266 A | 1/2000 | Segers et al. |
| 6,770,275 B1 | 8/2004 | Segers et al. |
| 6,783,764 B1 | 8/2004 | Segers et al. |
| 6,790,950 B2 | 9/2004 | Lowery et al. |
| 6,793,927 B1 | 9/2004 | Briggs et al. |
| 7,306,805 B2 | 12/2007 | Bakaletz et al. |
| 7,341,860 B2 | 3/2008 | Curtiss et al. |
| 7,351,416 B2 | 4/2008 | Briggs et al. |
| 7,449,178 B2 | 11/2008 | Crooke et al. |
| 7,476,391 B2 | 1/2009 | Lowery et al. |
| 7,763,262 B2 | 7/2010 | Lowery et al. |
| 2001/0018055 A1 | 8/2001 | Briggs et al. |
| 2003/0113845 A1 | 6/2003 | DeAngelis |
| 2004/0029129 A1 | 2/2004 | Wang et al. |
| 2004/0033586 A1 | 2/2004 | Crooke et al. |
| 2005/0106185 A1* | 5/2005 | Briggs ............... A61K 39/102 424/255.1 |
| 2009/0202594 A1 | 8/2009 | Lowery et al. |
| 2009/0246229 A1 | 10/2009 | Chang et al. |
| 2009/0252766 A1 | 10/2009 | Crooke et al. |
| 2010/0062017 A1 | 3/2010 | Luo |

FOREIGN PATENT DOCUMENTS

| WO | WO94/11024 | 5/1994 |
| WO | WO 99/51265 A1 | 10/1999 |
| WO | WO 02/075507 A2 | 9/2002 |
| WO | WO 03/086277 A2 | 10/2003 |
| WO | WO 2005/003330 A2 | 1/2005 |
| WO | WO 2008/118902 A1 | 10/2008 |
| WO | WO2010/002989 A2 | 1/2010 |
| WO | WO 2014/083091 | 6/2014 |

OTHER PUBLICATIONS

Tatum F M et al.: "Sialic acid uptake is necessary for virulence of Pasteurella multocida in turkeys", Microbial Pathogenesis, Academic Press Limited, New York, NY, US, val. 46, No. 6, Jun. 1, 2009 (Jun. 1, 2009), pp. 337-344, XP026161557.
Chung J Y et al.: "The Capsule Biosynthetic Locus of Pasteurella Multocida A1", FEMS Microbiology Letters, Wiley-Blackwell Publishing Ltd, GB, vol. 166, Sep. 15, 1998 (Sep. 15, 1998), pp. 289-296, XP002921439.
Fuller Troy E et al: Identification of Pasteurella multocida virulence genes in a septicemic mouse model using signature-tagged mutagenesis Microbial Pathogenesis, Academic Press Limited. New York, NY. US, vol. 29, No. 1. Jul. 1, 2000 (Jul. 1, 2000). 25-38, XP002202784.
W. Ding: "Analysis of the two active sites of the hyaluronan synthase and the chondroitin synthase of Pasteurella Multocida," Glycobiology, vol. 13, No. 10, Jun. 10, 2003 (Jun. 10, 2003, pp. 661-671, XP055168198.
Bagoes Poermadjaja et al.: "Phagocytic uptake and killing of virulent and avirulent strains of Pasteurella multocida of capsular serotype A by chicken macrophages," Veterinary Microbiology, vol. 72, No. 1-2, Mar. 1, 2000 (Mar. 1, 2000), pp. 163-171.

* cited by examiner

*Primary Examiner* — J. Hines
*Assistant Examiner* — Khatol Shahnan Shah
(74) *Attorney, Agent, or Firm* — Judy Jarecki-Black; Chad Kitchen; Merial Inc.

(57) ABSTRACT

The present invention provides attenuated *P. multocida* strains that elicit an immune response in animal *P. multocida*, compositions comprising said strains, methods of vaccination against *P. multocida*, and kits for use with such methods and compositions. The invention further provides novel, genetically-engineered mutations in *P. multocida* hyaD and nanPU genes, which are useful in the production of novel attenuated *P. multocida* bacterial strains.

14 Claims, 7 Drawing Sheets ively ATTENUATED PASTEURELLA MULTOCIDA
VACCINES AND METHODS OF MAKING
AND USE THEREOF This application claims priority to provisional application U.S. Ser. No. 61/898,497, filed on Nov. 1, 2013, and incorporated by reference herein in its entirety. All references cited herein, are incorporated by reference herein, in their entirety.

FIELD OF THE INVENTION

The present invention relates generally to attenuated bacterial vaccines, particularly those providing broad, safe, and effective protection to bovines against infections/disease caused by *Pasteurella Multocida*. The invention further relates to methods of producing the attenuated bacteria, and to the identification of nucleic acid variations that are associated with decreased virulence of the attenuated bacteria.

The invention accordingly relates to immunogenic or vaccine compositions comprising the bacteria of the invention; e.g., live attenuated bacteria. The bacteria also could be inactivated in the compositions; but it may be advantageous that the bacteria are live attenuated *P. multocida* bacteria. The invention therefore further relates to methods for preparing and/or formulating such compositions; e.g., culturing or growing or propagating the bacteria on or in suitable medium, harvesting the bacteria, optionally inactivating the bacteria, and optionally admixing the bacteria with a suitable veterinarily or pharmaceutically acceptable carrier, excipient, diluent or vehicle and/or an adjuvant and/or stabilizer. Thus, the invention also relates to the use of the bacteria in formulating such compositions.

BACKGROUND OF THE INVENTION

*Pasteurella multocida* is a gram-negative, non-motile, rod shaped, facultative anaerobe which is isolated from a wide range of animals and birds from all over the world.

The *P. multocida* isolates are classified into five serogroups (A, B, D, E and F) based on capsular antigens and 16 serotypes by somatic antigens (Rimler and Rhoades, 1989). Serogroup A is most commonly associated with fowl cholera in birds followed by serogroup D (Rhoades and Rimler, 1989). Among the isolates, serogroup F strains are predominantly isolated from poultry and turkeys, but rarely from calves (Shewen and Conlon, 1993; Catry et al., 2005). In pigs, atrophic rhinitis and pneumonia are primarily associated with serogroups D and A which express dermonecrotizing toxin (Dungworth, 1985). On the other hand *P. multocida* serogroups B and E are usually associated with hemorrhagic septicemia in cattle and water buffaloes in tropical and sub-tropical regions of Africa and Asia (Carter and de Alwis, 1989; Rimler and Rhoades, 1989; Shewen and Conlon, 1993). In contrast *P. multocida* serogroups B and E are rarely isolated North America cattle population (Confer, 1993). More than 92% of *P. multocida* isolated from the US cattle which cause severe suppurative bronchopneumonia belong to serotype A:3 (Ewers et al., 2006; Confer et al., 1996; Weekley et al., 1998). *P. multocida* infection in calves results in significant production yield losses and mortality (Ewers et al., 2006; Confer et al., 1996; Dalgleish, 1989; Weekley et al., 1998). Furthermore, *P. multocida* is often associated with bovine respiratory disease complex (BRDC) along with *Mannheima haemolytica* and *Histophilus somni*. From 2001, bovine pneumonic pasteurellosis due to *P. multocida* infection has increased in the UK cattle population. In many UK cases, *P. multocida* infections exceeded the number of outbreaks caused by *M. haemolytica* induced bovine bacterial pneumonia (Veterinary Laboratories Agency, 2007). Worldwide, *P. multocida* serogroup A isolates are one of the major pathogens associated with BRDC (Frank, 1989; Rimler and Rhoades, 1989).

*P. multocida* isolates associated with BRDC have numerous virulence or potential virulence and virulence-associated factors like adhesins and filamentous hemagglutinin which aid in adherence and colonization, iron acquisition proteins and transport systems, extracellular enzymes such as neuraminidase, endotoxin (lipopolysaccharide, LPS), polysaccharide capsule and a variety of outer membrane proteins (OMPs). Immunity of cattle against respiratory pasteurellosis is poorly understood; however some reports indicate that high serum antibodies against *P. multocida* OMPs are important for enhancing resistance against this bacterium.

There are a few commercial vaccines currently available against *P. multocida* for use in cattle. These vaccines are predominately traditional bacterins and a live streptomycin-dependent mutant. However, the field efficacy of these vaccines is questionable and none of the vaccines afford reliable protection. Therefore, there remains a need for safe and effective vaccines to protect cattle against *P. multocida* infections.

State of the Art Review

Intervet (Merck Animal Health) makes a hyaE gene-deleted *P. multocida* vaccine. In contrast, the instantly disclosed *P. multocida* vaccine is hyaD gene deletion mutant. HyaD is a different gene in the same locus, and although both the gene deletions result in an acapsular phenotype, a skilled person could not have predicted ahead of this disclosure whether deleting the hyaD gene would result in a stable, viable acapsular phenotype. Moreover, according to U.S. Pat. No. 7,351,416 B2 (Examples 3 & 4), the ΔhyaE vaccine may be administered to steers (weighing about 500 pounds), or 2-3 month old calves (weighing over 150 pounds). In contrast, the target animal for the vaccines of the instant disclosure are calves as young as 4-6 weeks old, and weighing significantly less. Immune responses of very young animals are significantly different than older ones. Furthermore, vaccine safety is of paramount importance when used in young calves.

EP1831248B1 (to Intervet) describes a transposon generated mutant *P. multocida*, which is not directed or site specific. Bacteria harboring such transposon insertions are not likely to be approved by regulatory agencies for use in vaccines, and so disclosure of these types of mutations may fairly be viewed as preliminary work leading to targeted gene modification, including deletion. The mutant gene is reported as "ORF 15," which is a membrane bound lysozyme inhibitor of c-type lysozyme. Finally, the vaccination challenge was done in poultry rather than calves.

WO2003086277A2 (to Merial) discloses attenuated *P. multocida* 1059. The gene deletions were initially produced using random signature tagged mutagenesis using transposon Tn5. Along with many specific and non-specific mutants, this library has mutants lacking PhyA, hyaC and hyaE genes which are involved with capsule biosynthesis. However, these mutants were generated by random mutagenesis and their genetic stability has not been tested over a long period. This is a critical property for a vaccine to be used as a modified live product under field conditions. Furthermore, *P. multocida* 1059 is an avian strain unsuitable for calf vaccination.

SUMMARY OF THE INVENTION

An object of this disclosure is to provide attenuated bacteria as well as methods for treatment and prophylaxis of infection by *P. multocida*.

The present disclosure further relates to efficacious field vaccines comprising attenuated *P. multocida* strains for use as vaccines in cattle. Mutant strains according to the instant disclosure may exhibit reduced or no expression of hyaD, nanPU genes, or both. Moreover, methods of producing the attenuated bacteria, as well as methods for providing cattle immunity, including protective immunity, against subsequent infections are disclosed herein. Kits comprising at least the attenuated *P. multocida* strain and instructions for use are also provided.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 1A shows the insertion of the hyaD-containing fragment into the pCR2.1 vector;

FIG. 1A shows the construction of the nanP/nanU fusion sequence-containing pCR2.1 vector from a fragment containing the full-length nanP and nanU sequences;

DETAILED DESCRIPTION OF THE INVENTION

Figure 1A:
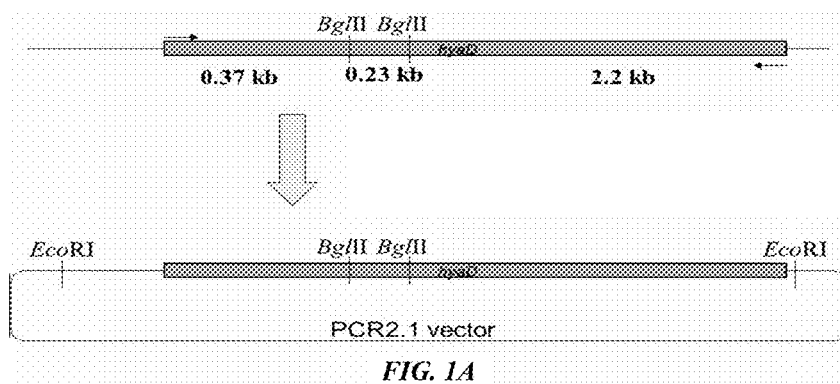
FIG. 1A is part of a flow diagram (FIGS. 1A-1F) showing the construction of the *P. multocida* 1062 hyaD mutant.

The present invention provides nucleotide sequences and genes involved in the attenuation of a microorganism, such as bacteria, for instance, Gram negative bacteria, e.g., *Pasteurella multocida* (*P. multocida*), products (e.g., proteins, antigens, immunogens, epitopes) encoded by the nucleotide sequences, methods for producing such nucleotide sequences, products, micro-organisms, and uses therefor, such as for preparing vaccine or immunogenic compositions or for eliciting an immunological or immune response or as a vector, e.g., as an expression vector (for instance, an in vitro or in vivo expression vector).

In order to develop an efficacious *P. multocida* field vaccine, three attenuated strains were genetically engineered: 1) a hyaD partial deletion mutant, which is unable to synthesize glycosyl transferase, and so exhibits the acapsular phenotype; 2) a nanPU deletion, which is unable to add sialic acid residues to terminal lipooligosaccharides; and 3) a double knockout mutant lacking both hyaD and nanPU genes.

Mutations, including deletions and partial deletions, introduced into nucleotide sequences and genes of micro-organisms produce novel and nonobvious attenuated mutants. These mutants are useful for the production of live attenuated immunogenic compositions or live attenuated vaccines having a high degree of immunogenicity.

These mutants are also useful as vectors which can be useful for expression in vitro of expression products, as well as for reproduction or replication of nucleotide sequences (e.g., replication of DNA), and for in vivo expression products.

Identification of the mutations provides novel and nonobvious nucleotide sequences and genes, as well as novel and nonobvious gene products encoded by the nucleotide sequences and genes.

Such gene products provide antigens, immunogens and epitopes, and are useful as isolated gene products.

Such isolated gene products, as well as epitopes thereof, are also useful for generating antibodies, which are useful in diagnostic applications.

Such gene products, which can provide or generate epitopes, antigens or immunogens, are also useful for immunogenic or immunological compositions, as well as vaccines.

In an aspect, the invention provides bacteria containing an attenuating mutation in a nucleotide sequence or a gene wherein the mutation modifies, reduces or abolishes the expression and/or the biological activity of a polypeptide or protein encoded by a gene, resulting in attenuated virulence of the bacterium.

The mutation need not be located within a coding sequence or gene to disrupt its function, leading to attenuation. The mutation can also be made in nucleotide sequences involved in the regulation of the expression of the gene, for instance, in regions that regulate transcription initiation, translation and transcription termination. Thus also included are promoters and ribosome binding regions (in general these regulatory elements lie approximately between 60 and 250 nucleotides upstream of the start codon of the coding sequence or gene; Doree S M et al., J. Bacteriol. 2001, 183(6): 1983-9; Pandher K et al., Infect. Imm. 1998, 66(12): 5613-9; Chung J Y et al., FEMS Microbiol letters 1998, 166: 289-296), transcription terminators (in general the terminator is located within approximately 50 nucleotides downstream of the stop codon of the coding sequence or gene; Ward C K et al., Infect. Imm. 1998, 66(7): 3326-36). In the case of an operon, such regulatory regions may be located in a greater distance upstream of the gene or coding sequence. A mutation in an intergenic region can also lead to attenuation.

A mutation within such regulatory sequences associated with the coding sequence or gene so that the mutation of this nucleotide sequence modifies, inhibits or abolishes the expression and/or the biological activity of the polypeptide or the protein encoded by the gene, resulting in attenuated virulence of the bacterium would be an equivalent to a mutation within a gene or coding sequence identified in the present invention Attenuation reduces or abolishes the pathogenicity of the bacteria and the gravity of the clinical signs or lesions, decreases the growth rate of the bacteria, and prevents the death from the bacteria.

In particular, the present invention encompasses attenuated P. multocida strains and vaccines comprising the same, which elicit an immunogenic response in an animal, particularly the attenuated P. multocida strains that elicit, induce or stimulate a response in a bovine.

Particular P. multocida attenuated strains of interest have mutations in genes, relative to wild type virulent parent strain, which are associated with virulence. It is recognized that, in addition to strains having the disclosed mutations, attenuated strains having any number of mutations in the disclosed virulence genes can be used in the practice of this invention.

In an embodiment, the attenuated strains comprise mutations in nucleic acid sequences comprising the nucleotides as set forth in SEQ ID NOs:1, 5, or both. The attenuated strains may also comprise mutations in sequences having at least 70% identity to the sequences as set forth in SEQ ID NOs:1, 5, or both, with the proviso that the homologous sequences must encode homologous proteins having comparable functions to those encoded by SEQ ID NO:1 or 5. Examples of comparable functions include the ability to catalyze the same enzymatic reaction and the ability to serve the same structural role. The attenuated strains may also comprise mutations in sequences having at least 75%, 80%, 85%, 90%, 95%, 96%, 97%, 98%, or 99% identity to the sequences as set forth in SEQ ID NOs:1, 5, or both, with the same proviso.

In an embodiment, the attenuated strains may comprise sequences having at least 75%, 80%, 85%, 90%, 95%, 96%, 97%, 98%, or 99% identity to the sequences as set forth in SEQ ID NOs:11, 12, or both, provided that the homologous sequences result in the attenuated phenotype, wherein the attenuated strains are comparably capable of safely eliciting an immune response relative to attenuated strains comprising the sequences as set forth in SEQ ID NOs:11, 12, or both. The skilled person understands well that the attenuated strains comprise the mutated sequence(s) in place of the wild-type sequence(s). Thus, it is not intended that the invention should encompass, for example, a strain comprising both SEQ ID NO:1 (wild-type) and SEQ ID NO:3 (mutated). However, the inventors do envision that any deletion/modification of either or both SEQ ID NO:1 and SEQ ID NO:5 may transform a virulent P. multocida strain into an attenuated strain, according to the instant disclosure.

In another embodiment, the attenuated P. multocida strains comprise nucleic acids encoding a peptide having the sequence as set forth in SEQ ID NOs:4, 13, or a peptide having 80%, 85%, 90%, 95%, or 98% homology thereto, and having comparable function thereto. In yet another embodiment, the strains comprise nucleic acids encoding peptides having at least one amino acid substitution with respect to the sequences as set forth in SEQ ID NOs:4, 13, or both.

At the time of this disclosure, the mutants described herein were not known to exist in any naturally-occurring P. multocida genomes, and were only produced as a result of the disclosed mutagenesis methods.

In yet another embodiment, the attenuated P. multocida strain has mutations in the same genes, relative to its virulent parental strain, as the strain deposited at the American Type Culture Collection (ATCC®), in accordance with the Budapest Treaty, under the Patent Deposit Designation PTA-120624 (i.e. P. mult.1062 Nan May 9, 2012). The PTA-120624 attenuated P. multocida strain was deposited on Oct. 16, 2013, at the ATCC® depository located in Manassas, Va. (ie, 10801 University Blvd, Manassas, Va. 20110), These mutations result in the attenuated strain having reduced virulence relative to it virulent parental strain.

In a particular embodiment, the attenuated strain is the strain deposited at the ATCC under the Patent Deposit Designation PTA-120624 (i.e. P. mult.1062 Nan May 9, 2012).

In another aspect, the novel attenuated P. multocida strains are formulated into safe, effective vaccine against P. multocida and infections/diseases cause by P. multocida.

In an embodiment, the P. multocida vaccines further comprise an adjuvant. In a particular embodiment, the adjuvant is a mucosal adjuvant, such as chitosan, methylated chitosan, trimethylated chitosan, or derivatives or combinations thereof.

In an embodiment, the adjuvant comprises whole bacteria and/or viruses, including H. parasuis, clostridium, swine influenza virus (SIV), bovine circovirus (PCV), bovine reproductive and respiratory syndrome virus (PRRSV), Mannheimia, Pasteurella, Histophilus, Salmonella, Escherichia coli, or combinations and/or variations thereof. In several embodiments, the adjuvant increases the animal's production of IgM, IgG, IgA, and/or combinations thereof.

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), bovine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Compositions

The present invention relates to a *P. multocida* vaccine or composition which may comprise an attenuated *P. multocida* strain and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of Use and Article of Manufacture

The present invention includes the following method embodiments. In an embodiment, a method of vaccinating an animal comprising administering a composition comprising an attenuated *P. multocida* strain and a pharmaceutical or veterinarily acceptable carrier, excipient, or vehicle to an animal is disclosed. In one aspect of this embodiment, the animal is a bovine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of cow or bovine compositions, based on bacterial antigens, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as bovines, with a virulent strain of *P. multocida*. Both homologous and heterologous strains are used for challenge to test the efficacy of the vaccine. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of *P. multocida*-specific antibody.

The compositions comprising the attenuated bacterial strains of the invention used in the prime-boost protocols are contained in a pharmaceutically or veterinary acceptable vehicle, diluent or excipient. The protocols of the invention protect the animal from *P. multocida* and/or prevent disease progression in an infected animal.

The various administrations are preferably carried out 1 to 6 weeks apart. Preferred time interval is 3 to 5 weeks, and optimally 4 weeks according to one embodiment, an annual booster is also envisioned. The animals, for example pigs, may be at least 3-4 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against *P. multocida* in an animal comprising an attenuated *P. multocida* immunological composition or vaccine and instructions for performing the method of delivery in an effective amount for eliciting an immune response in the animal.

Another embodiment of the invention is a kit for performing a method of inducing an immunological or protective response against *P. multocida* in an animal comprising a composition or vaccine comprising an attenuated *P. multocida* strain of the invention, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912).

In an embodiment, the adjuvant may be inactivated bacteria, an inactivated virus, fractions of inactivated bacteria, bacterial lipopolysaccharides, bacterial toxins, or derivatives or combinations thereof.

In an embodiment, the adjuvant comprises whole bacteria and/or viruses, including *H. parasuis*, clostridium, swine immunodeficiency virus (SIV), bovine circovirus (PCV), bovine reproductive and respiratory syndrome virus (PRRSV), *Mannheimia, Pasteurella, Histophilus, Salmonella, Escherichia coli*, or combinations and/or variations thereof. In several embodiments, the adjuvant increases the animal's production of IgM, IgG, IgA, and/or combinations thereof.

REFERENCES

Rimler R B and Rhoades K R (1989). *Pasteurella multocida*. In: Adlam C and Rutter J M (eds) *Pasteurella* and Pasteurellosis. London: Academic Press, pp. 37-73.

Rhoades K R and Rimler R B (1989). Fowl Cholera. London: Academic Press

Catry B, Chiers K, Schwarz S, Kehrenberg C, Decostere A and de Kruif A (2005). Fatal peritonitis caused by *Pasteurella multocida* capsular type F in calves. Journal of Clinical Microbiology 43: 1480-1483.

Dungworth D C (1985). The respiratory system. In: Jubb K V F, Kennedy P C and Palmer N (eds) Pathology of Domestic Animals, Orlando, Fla.: Academic Press, pp. 448-489.

Carter G R and de Alwis M C L (1989). Hemorrhagic septicemia. In: Adlam C and Rutter J M (eds) *Pasteurella* and Pasteurellosis. London: Academic Press, pp. 132-160.

Shewen P E and Conlon J A R (1993). *Pasteurella*. In: Gyles C L and Thoen C O (eds) Pathogenesis of Bacterial Infections in Animals. Ames, Iowa: Iowa State University Press, pp. 216-225.

Confer A W (1993). Immunogens of *Pasteurella*. Veterinary Microbiology 37: 353-368.

Confer A W, Nutt S H, Dabo S M, Panciera R J and Murphy G L (1996). Antibody responses of cattle to outer membrane proteins of *Pasteurella multocida* A:3. American Journal of Veterinary Research 57: 1453-1457

Dalgleish R (1989) Studies on Experimental Pneumonia Pasteurellosis in Calves. PhD thesis, University of Glasgow.

Ewers C, Lubke-Becker A, Bethe A, Kiebling S, Filter M and Wieler L H (2006). Virulence genotype of *Pasteurella multocida* strains isolated from different hosts with various disease status. Veterinary Microbiology 114: 304-317.

Weekley L B, Veit H P, Eyre P (1998) Bovine pneumonic pasteurellosis. Part I. Pathophysiology. Compendium on Continuing Education for the Practicing Veterinarian, 20, S33eS46.

Veterinary Laboratories Agency. (2007) VIDA 2007, Yearly Trends, Cattle. http://www.defra.gov.uk/vla/reports/rep_vida07.htm.

Frank G H (1989). Pasteurellosis of cattle. In: Adlam C and Rutter J M (eds) *Pasteurella* and Pasteurellosis, London: Academic Press, pp. 197-222.

Tatum F M, Tabatabai L B, Briggs R E. 2009. Sialic acid uptake is necessary for virulence of *Pasteurella multocida* in turkeys. Microb Pathog. 46(6):337-344.

Steenbergen S M, Lichtensteiger C A, Caughlan R, Garfinkle J, Fuller T E, Vimr E R. 2005. Sialic Acid metabolism and systemic pasteurellosis. Infect Immun. 73(3): 1284-1294.

Briggs, R. E., Tatum, F. M. 2005. Generation and molecular characterization of new temperature-sensitive plasmids intended for genetic engineering of Pasteurellaceae. Appl Environ Micobiol 71:7187-7195.

Chung J Y, Zhang Y, Adler B., 1998. The capsule biosynthetic locus of *Pasteurella multocida* A:1. FEMS Microbiol Lett. 166(2):289-296.

Lawrence, P. K., Shanthalingam, S., Dassanayake, R. P., Subramaniam, R., Herndon, C. N., Knowles, D. P., Foreyt, W. J., Wayman, G., Marciel, A. M., Highlander, S. K., Srikumaran, S. 2010. Transmission of *Mannheimia haemolytica* from domestic sheep (*Ovis aries*) to bighorn sheep (*Ovis canadensis*): unequivocal demonstration with green fluorescent protein-tagged organisms. Journal of Wildlife Disease. 46 (3): 706-717.

The invention will now be further described by way of the following non-limiting examples.

EXAMPLES

Example 1

Development of *P. multocida* hyaD Mutant Strain and Characterization of Master Seed A *P. multocida* mutant of strain 1062, unable to synthesize capsule (acapsular), was constructed by deleting a portion of the coding region of hyaD and thereby inactivating the synthesis of glycosyl transferase (Chung et al., 1998). The acapsular mutant was created by following the published protocol (Briggs and Tatum 2005). The majority of the coding regions of *P. multocida* 1062 hyaD was obtained by PCR amplification, using the forward primer 5'-ATG ATA TTT GAG AAG TCG GCG G-3' (SEQ ID NO:14) and the reverse primer 5'-TGT AAT TTT CGT TCC CAA GGC-3' (SEQ ID NO:15) (Briggs, R. E., Tatum, F. M. 2005). These two primers were synthesized with an oligonucleotide synthesizer (Applied Biosystems Inc., CA) by Integrated DNA Technologies, Inc., Coralville, Iowa. The PCR reactions were carried out using the GeneAmp LX PCR Kit (PE Applied Biosystems, Foster City, Calif.) in a Perkin Elmer GeneAmp 9600 thermocycler. Reaction conditions were 30 cycles, each consisting of 30 seconds at 95° C., 45 seconds at 54° C., and 90 seconds at 72° C.

The PCR-generated hyaD fragment used here extended from the starting methionine codon and ended 85 base pairs upstream of the stop codon. The fragment was inserted into pCR2.1 (Invitrogen Inc., LaJolla, Calif.) and the recombinant plasmid was electroporated into the *E. coli* strain DH11S (Life Technologies, Rockville, Md.) thus generating the plasmid, pCR2.1hyaDPm1062. This plasmid was isolated from *E. coli* by the alkaline SDS method and purified by CsCl centrifugation using standard methods. Both strands of the hyaD gene were sequenced using the Dye Terminator Chemistry kit from PE Applied Biosystems and samples were run on an ABI Prism 377 DNA Sequencer by the Nucleic Acids Facility, Iowa State University, Ames, Iowa.

The precise deletion within hyaD was produced by treating plasmid, pCR2.1hyaDPm1062 with the restriction enzyme BglII. This treatment produced a 225 bp deletion within hyaD which upon ligation resulted in an in-frame deletion. The deleted hyaD fragment was transferred into the EcoRI site within the multiple cloning site of plasmid pBCSK (Strategene Inc.) to produce pBCSKΔhyaDPm1062. Next, the Tn903 kanamycin resistance element (GenBlock) was inserted into the adjacent SalI site to produce pBCSKΔhyaDPm1062kan$^R$. Construction of the replacement plasmid was completed by ligating BssHII digested pBCSKΔhyaDPm1062kan$^R$ to the 1.2 kb temperature-sensitive origin of replication of the plasmid, pCT109GA189 (Briggs and Tatum, 2005). Because the ColE1 origin is inactive in *P. multocida*, only the ligation product generating plasmid, pCT109GA189ΔhyaDPm1062kan$^R$, was capable of replicating within *P. multocida* strain 1062.

Replacement plasmid, pCT109GA189ΔhyaDPm1062kan$^R$ was introduced into *P. multocida* strain 1062 as follows. Cells were grown in Columbia broth to a density of $OD_{600}$=0.5. The cells were chilled on ice for 10 min and pelleted by centrifugation at 5000×g for 15 min. The cells were resuspended in ice-cold distilled water and pelleted as described above. A second wash was done and the cell pellet was resuspended 1:3 (bacteria:water) and placed on ice. The competent bacteria (100 μl) were mixed in a 0.1 cm electroporation cuvette (Bio-Rad) with the replacement plasmid ligation mixture. Immediately after adding DNA, the cells were electroporated (Gene pulser, Bio-Rad) at 18,000 V/cm, 800 ohm, and 25 mFd, with resultant time constants ranging from 11 to 15 msec.

Chilled Columbia broth (1 ml) was added to the electroporated cells, and the suspension was incubated at 25° C. for approximately 2 hours. The cells were then plated onto Columbia blood agar plates containing 50 μg/ml kanamycin. Colonies were visible after 24 hour incubation at 30° C. Colonies were transferred to 2 ml of Columbia broth containing 50 μg/ml kanamycin and incubated overnight at 30° C. The next day, approximately 20 μl of the culture was spread onto dextrose starch agar plates containing 50 μg/ml kanamycin and incubated at 38° C., the nonpermissive temperature for the replacement plasmid. Cells possessing integrated replacement plasmid survived antibiotic selection at the non-permissive temperature for plasmid replication (38° C.). These single-crossover mutants could be easily identified phenotypically because integration of replacement plasmid into hyaD of the host resulted in loss of capsule. Wild-type capsular colonies of *P. multocida* 1062 possess hyaluronic acid, the major capsule component, are mucoid in appearance and when viewed under obliquely transmitted light exhibit a pearl-like iridescence. In contrast, the acapsular single-crossover mutants are non-mucoid and non-iridescent.

Figure 1B:
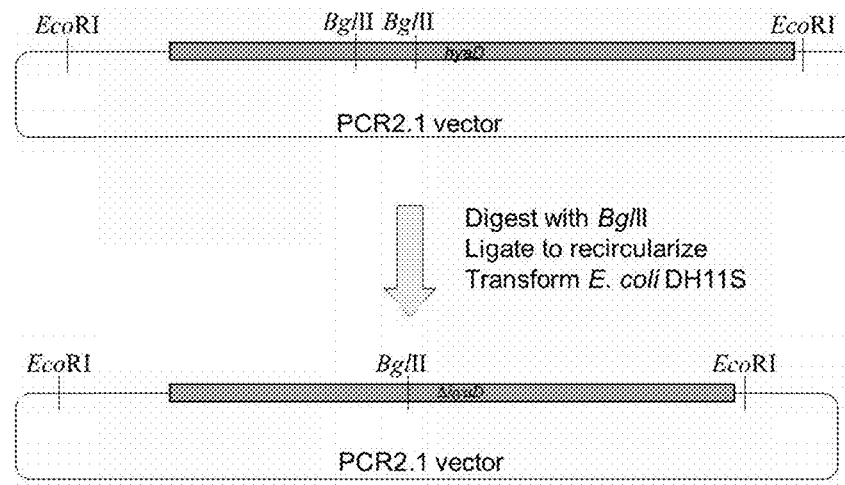
FIG. 1B depicts the removal of the BglII fragment to produce the ΔhyaD-containing pCR2.1 vector.
Figure 1C:
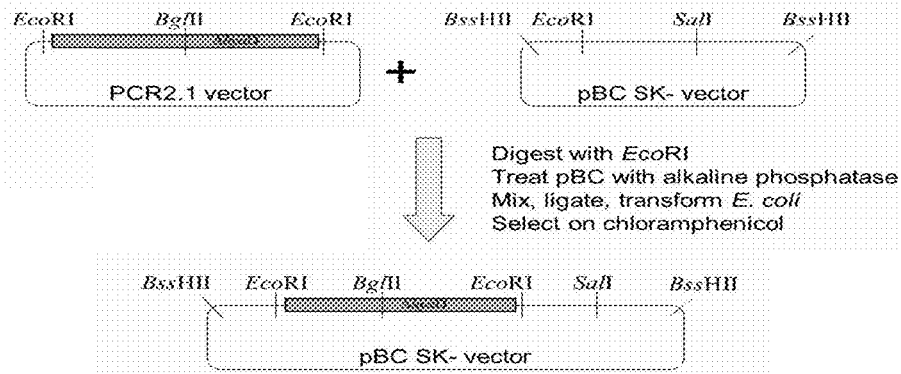
FIG. 1C depicts the shuttling of the ΔhyaD-containing fragment into the pBC SK-vector.
Figure 1D:
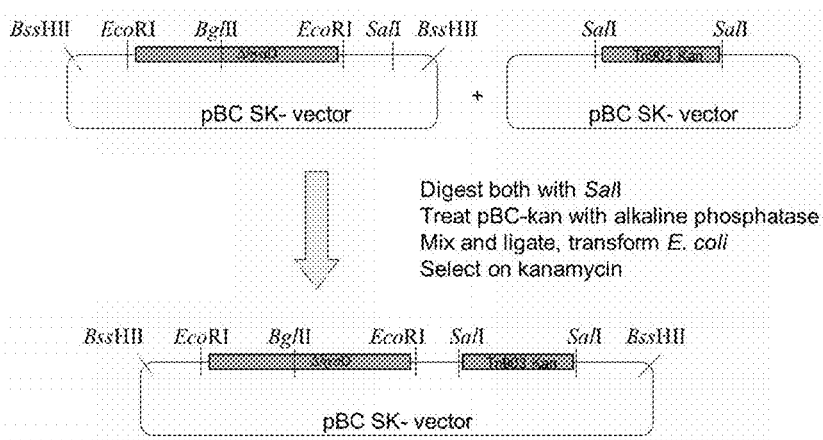
FIG. 1D depicts the insertion of the Tn903 Kan-containing SalI fragment into the ΔhyaD-containing pBC SK-vector.
Figure 1E:
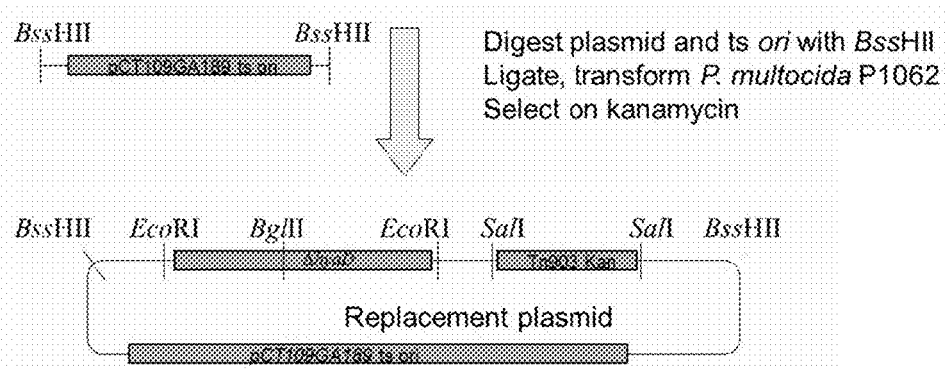
FIG. 1E depicts the insertion of the pCT109GA189 ts on into the ΔhyaD- and Tn903 Kan-containing pBC SK-vector, to form the "replacement" vector.
Figure 1F:
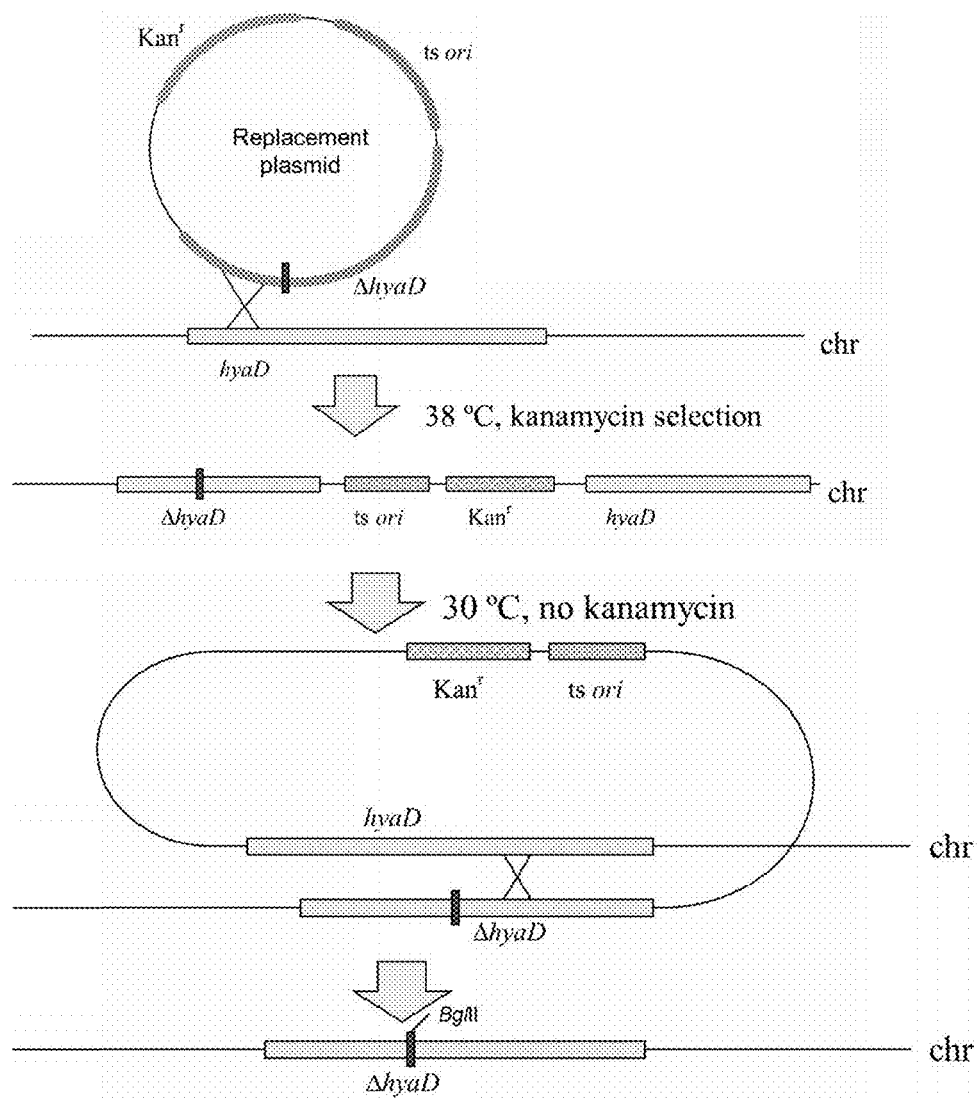
FIG. 1F depicts the replacement of the genomic hyaD sequence with the ΔhyaD sequence.
Figure 2:
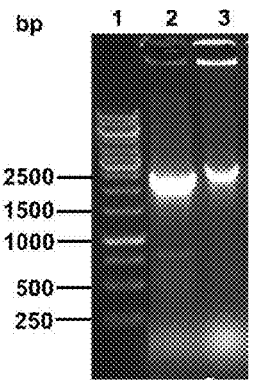
FIG. 2 is a gel image showing the hyaD-specific PCR products amplified from the *P. multocida* 1062 hyaDΔ-4PKL strain (lane 2) and the virulent parental *P. multocida* 1062 wild type strain (lane 3)

Several single-crossover mutants, possessing integrated replacement plasmid, were transferred to 5 ml Columbia broth without antibiotic supplementation and incubated at 30° C. overnight. The next day, approximately 2 μl of growth was transferred to fresh 5 ml Columbia broth (without antibiotic) and incubated overnight at 30° C. This process was repeated several more times to allow for the resolution of the plasmid and mutant formation. After 5 such passages, cells were transferred to dextrose-starch agar plates without supplemental antibiotic and incubated at 38° C. for 16 hours. The colonies which arose on the non-selection plates consisted of both capsular and acapsular phenotypes. These results were expected; depending on where replacement-plasmid resolution occurred either wild-type or mutant colonies were generated. The initial test to identify double crossover mutants (i.e. acapsular hyaD mutants) involved replica-plating acapsular colonies onto dextrose starch agar plates with and without antibiotic followed by overnight incubation at 38° C. Kanamycin sensitive acapsular colonies were further analyzed by PCR using the hyaD primers described previously. The PCR products of the putative hyaD mutants were compared to those of the wild-type parent using agarose gel electrophoresis. PCR products that were of the expected size were sequenced using the hyaDF (5'-ATG ATA TTT GAG AAG TCG GCG G-3' (SEQ ID NO:14)) and hyaDR (5'-GTA ATT TTC GTT CCC AAG GC-3' (SEQ ID NO:15)) primers. Moreover, the putative hyaD mutants were analyzed by PCR for the absence of temperature sensitive plasmid origin of replication of pCT109GA189 and for the absence of the Tn903 kanamycin resistance element. A flow diagram showing the construction of *P. multocida* 1062 hyaD mutant is shown in FIG. 1 (steps A-F).

A lyophilized culture of the mutant *P. multocida* 1062 (serotype A:3) was obtained from NADC, Ames Iowa. The lyophilized powder was rehydrated using sterile distilled water and streaked on TSA plates supplemented with 5% sheep blood and incubated at 37° C. overnight. The next day, three individual colonies were picked and colony PCR was performed using hyaDF and hyaDR primers as described earlier (Lawrence et al., 2010). The clones as expected, amplified a band at 2.691 kb, when compared to the parent strain (2.916 kb), indicating a truncated hyaD gene. A single colony from one of the clones was inoculated into autoclaved brain heart infusion (BHI) medium and incubated at 37° C./200 rpm overnight. The next day, cultures were diluted to 0.4 OD (optical density at 600 nm) in BHI broth and allowed to grow until log phase. Once the cultures reached log phase ($OD_{600}$=0.8), an equal volume of 50% sterile glycerol was added, mixed and aliquoted into 2 ml cryovials. The master seed was frozen at a concentration of $2.6\times10^9$ CFU/ml. The vials were labeled as *P. multocida* 1062 hyaDΔ-4PKL and stored at −70° C. at Newport Laboratories Research and Development, located at 1810 Oxford Street, Worthington, Mn-56187.

The master seed stock was seeded onto TSA plates supplemented with 5% sheep blood, and a single colony was picked to confirm the presence of truncated hyaD by PCR (FIG. 2). The master seed was sent to internal quality control (QC) laboratory for sterility testing according to 9CFR 113.27(b), and was devoid of any extraneous (fungal) growth. A TSA plate containing *P. multocida* 1062 hyaDΔ-1PKL was obtained from the QC laboratory and sent to internal diagnostics laboratory for identification/confirmation according to 9CFR 113.64(c)4. After confirming that the growth obtained from the QC laboratory was mutant *P. multocida* 1062 hyaDΔ-1PKL, we analyzed a single colony from the TSA plate again for the presence of truncated hyaD gene by PCR. The master seed was tested for safety in outbred mice [Hsd:ICR (CD-1®), Harlan], per 9CFR 113.33 and was found to be safe.

The master seed stock was seeded onto TSA plates supplemented with 5% sheep blood, and a single colony was picked and colony PCR was performed as described earlier (Lawrence et al., 2010) using hyaDF and hyaDR primers. The agarose gel image is shown in FIG. Lanes: 1—molecular weight marker; 2—PCR product of *P. multocida* 1062 hyaDΔ-4PKL showing truncated hyaD gene (2.691 kb); 3—PCR product of *P. multocida* 1062 wild type showing full length hyaD gene (2.916 kb).

Example 2 nanPU Mutant Strain Development and Master Seed Characterization

A *P. multocida* mutant of strain 1062, unable to add sialic acid residues to lipooligosaccharide (LOS) molecules, was constructed by deleting a portion of the coding region of nanPU and thereby inactivating the synthesis of a sialic acid transferase enzyme complex (Tatum et al., 2009; Steenbergen et al., 2005). The locus nanP encodes a sialic acid-binding periplasmic protein SiaP and the locus nanU encodes sialic acid TRAP transporter permease protein SiaT-23. The sialic acid deficient mutant was created by following the published protocol (Briggs and Tatum 2005). The coding regions of nanP and nanU of *P. multocida* 1062 were obtained by PCR amplification, using the forward and reverse primers 1062nanPU_F 5'-TTC CCT AGC TCA CAG TTA GGT GAT-3' (SEQ ID NO:6)/1062nanPU_delR 5'-GTC ACA CCT TGA CTT TTG AAG AAT TCA-3' (SEQ ID NO:7); and 1062nanPU_delF 5'-AAT TCC AAT TGC GGT TCA CTT TGG CA-3' (SEQ ID NO:8)/1062nanPU_R 5'-TCT GCA ATT TCT TTC CAT TCT TTT GGA-3' (SEQ ID NO:9), respectively (FIG. 3A). The PCR reactions were carried out using the GeneAmp LX PCR Kit (PE Applied Biosystems, Foster City, Calif.) in a Perkin Elmer GeneAmp 9600 thermocycler. Reaction conditions were 30 cycles, each consisting of 30 seconds at 95° C., 45 seconds at 54° C., and 90 seconds at 72° C.

The PCR-generated nanP and nanU fragments were digested with EcoRI and MunI respectively, ligated and cloned into PCR2.1 vector (Invitrogen Inc., LaJolla, Calif.). The recombinant plasmid was electroporated into the *E. coli* strain DH11S (Life Technologies, Rockville, Md.) thus generating the plasmid, pCR2.1nanPUPm1062. This plasmid was isolated from *E. coli* by the alkaline SDS method and purified by CsCl centrifugation using standard methods. Both strands of the nanPU gene were sequenced using the Dye Terminator Chemistry kit from PE Applied Biosystems and samples were run on an ABI Prism 377 DNA Sequencer by the Nucleic Acids Facility, Iowa State University, Ames, Iowa.

The deleted nanPU fragment was transferred into the EcoRI site within the multiple cloning site of plasmid pBCSK (Strategene Inc.,) to produce pBCSKΔnanPUPm1062 (FIG. 1B). Next, the Tn903 kanamycin resistance element (GenBlock) was inserted into the adjacent SalI site to produce pBCSKΔnanPUPm1062kanR. Construction of the replacement plasmid was completed by ligating BssHII digested pBCSKΔnanPUPm1062kanR to the 1.2 kb temperature-sensitive origin of replication of plasmid, pCT109GA1894 (Briggs and Tatum, 2005). Because the ColE1 origin is inactive in *P. multocida*, only the ligation product generating plasmid, pCT109GA189ΔnanPUPm1062kanR, was capable of replicating within *P. multocida* strain 1062 (FIGS. 3C & D).

Replacement plasmid, pCT109GA189ΔnanPUPm1062kanR was introduced into *P. multocida* strain 1062 as follows. Cells were grown in Columbia broth to a density of OD600=0.5. The cells were chilled on ice for 10 min and pelleted by centrifugation at 5000×g for 15 min. The cells were resuspended in ice-cold distilled water and pelleted as described above. A second wash was done and the cell pellet was resuspended 1:3 (bacteria:water) and placed on ice. The competent bacteria (100 μl) were mixed in a 0.1 cm electroporation cuvette (Bio-Rad) with the replacement plasmid ligation mixture. Immediately after adding DNA, the cells were electroporated (Gene pulser, Bio-Rad) at 18,000 V/cm, 800 ohm, and 25 mFd, with resultant time constants ranging from 11 to 15 msec.

Chilled Columbia broth (1 ml) was added to the electroporated cells, and the suspension was incubated at 25° C. for approximately 2 hours. The cells were then plated onto Columbia blood agar plates containing 50 μg/ml kanamycin. Colonies were visible after 24 hour incubation at 30° C. Colonies were transferred to 2 ml of Columbia broth containing 50 μg/ml kanamycin and incubated overnight at 30° C. The next day, approximately 20 μl of the culture was spread onto dextrose starch agar plates containing 50 μg/ml kanamycin and incubated at 38° C., the nonpermissive temperature for the replacement plasmid. Cells possessing integrated replacement plasmid survived antibiotic selection at the non-permissive temperature for plasmid replication (38° C.).

Figure 3A:
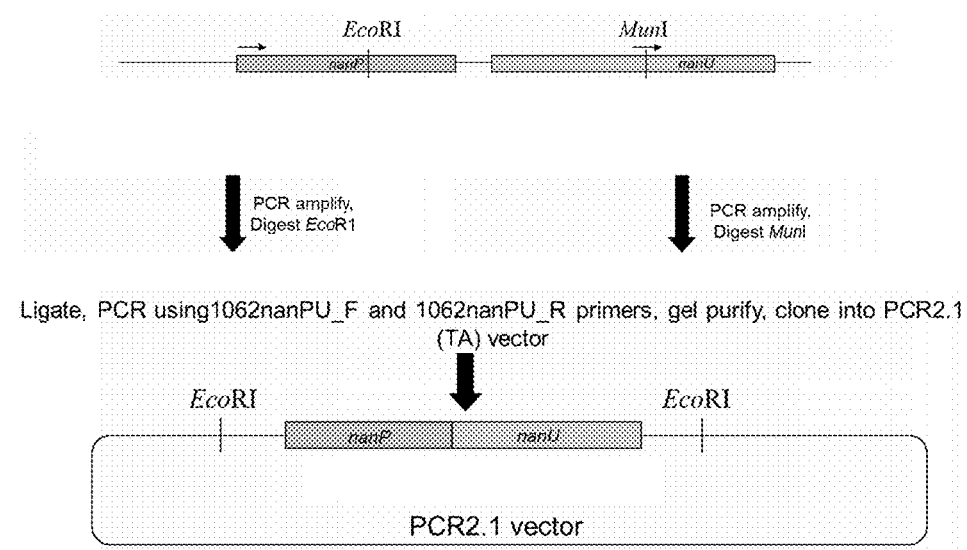
FIG. 3A is part of a flow diagram (FIGS. 3A-3F) showing the construction of the *P. multocida* 1062 nanPU mutant.
Figure 3B:
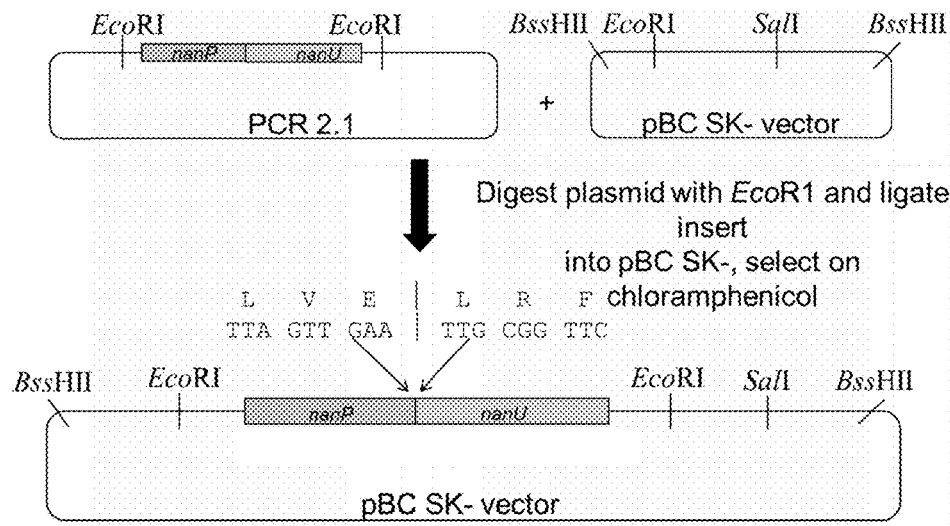
FIG. 3B depicts the insertion of the nanP/nanU fusion sequence into the pBC SK-vector.
Figure 3C:
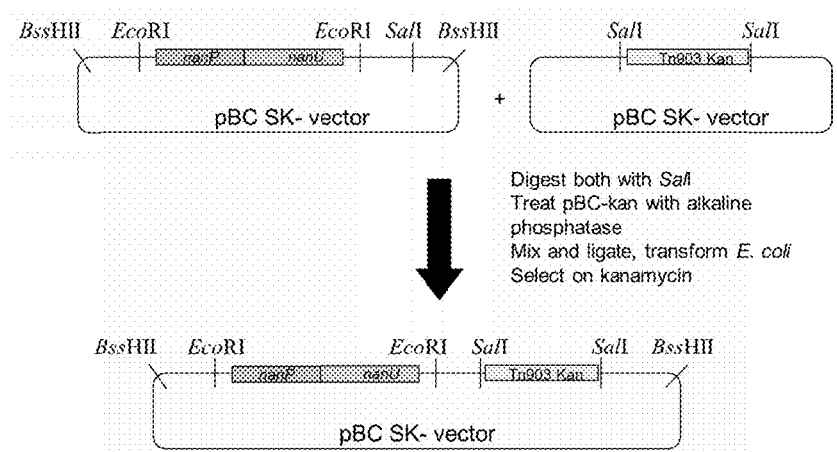
FIG. 3C depicts the insertion of the Tn903 Kan-containing SalI fragment into the nanPU fusion-containing pBC SK-vector.
Figure 3D:
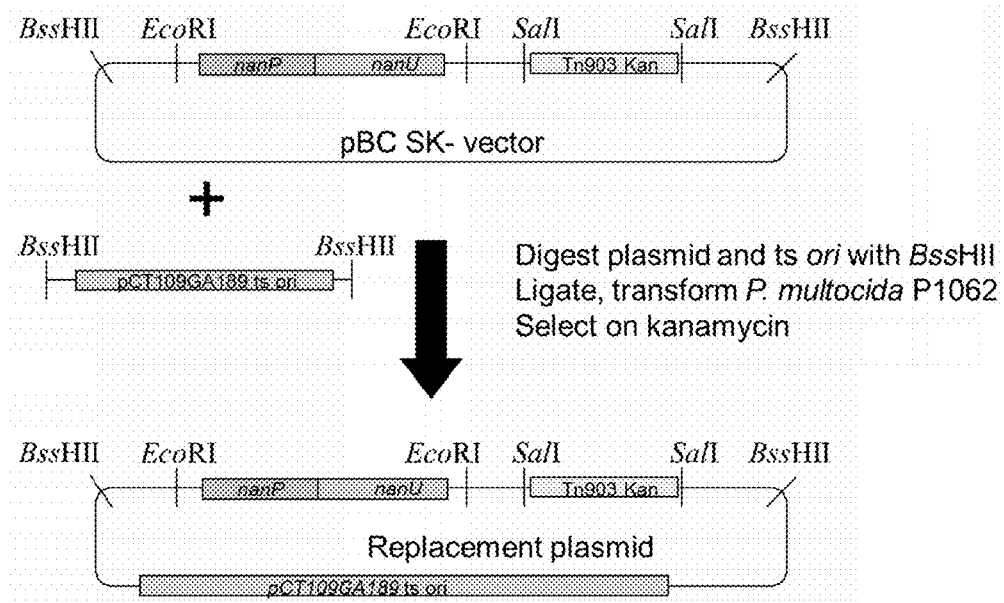
FIG. 3D depicts the insertion of the pCT109GA189 ts on into the nanPU fusion- and Tn903 Kan-containing pBC SK-vector, to form the "replacement" vector.
Figure 3E:
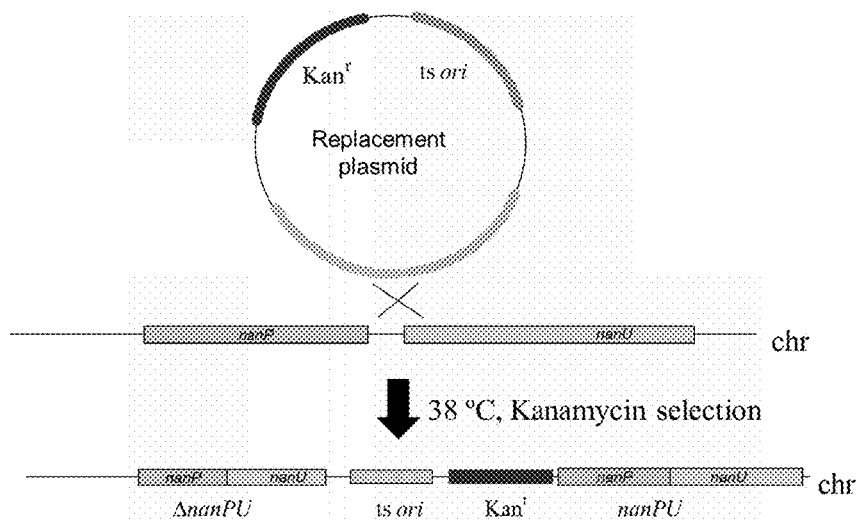
FIG. 3E depicts the integration of the replacement plasmid into the chromosome.
Figure 3F:
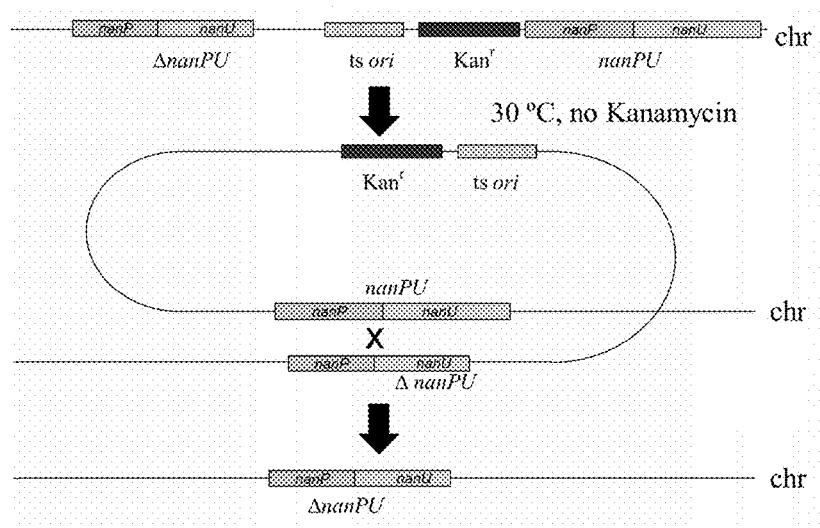
FIG. 3F depicts the resolution of the replacement plasmid from the chromosome.
Figure 4:
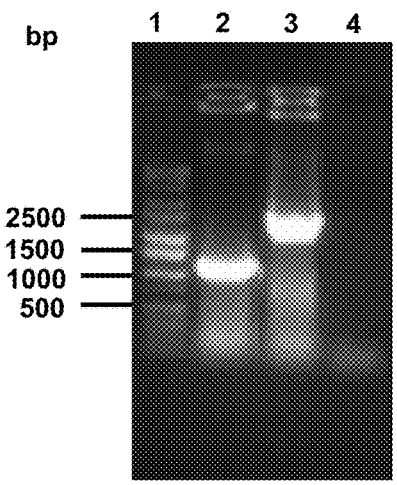
FIG. 4 is a gel image showing the nanPU-specific PCR products amplified from the *P. multocida* 1062 truncated nanPU strain (lane 2) and the virulent parental *P. multocida* 1062 wild type strain (lane 3)
Figure 5:
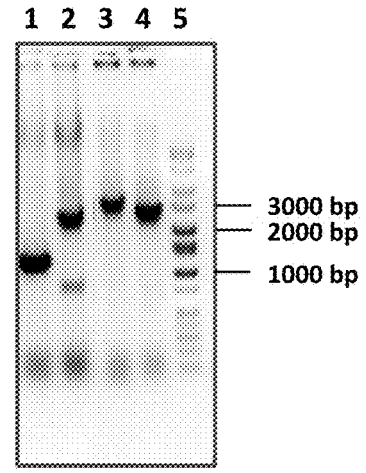
FIG. 5 is a gel image showing 1) *P. multocida* ΔnanPU/HyaD mutant amplified with nanPUF/nanPUR primers (1.3 Kb); 2) *P. multocida* ΔnanPU/HyaD mutant amplified with hyaDF/hyaDR primers (2.691 Kb); 3) *P. multocida* 1062 wild type amplified with nanPUF/nanPUR primers (3.150 Kb); and 4) *P. multocida* 1062 wild type amplified with hyaDF/hyaDR primers (2.916 Kb)

Several single-crossover mutants, possessing integrated replacement plasmid, were transferred to 5 ml Columbia broth without antibiotic supplementation and incubated at 30° C. overnight. The next day, approximately 2 μl of growth was transferred to fresh 5 ml Columbia broth (without antibiotic) and incubated overnight at 30° C. This process was repeated several more times to allow for the resolution of the plasmid and mutant formation. After 5 such passages, cells were transferred to dextrose-starch agar plates without supplemental antibiotic and incubated at 38° C. for 16 hours. The colonies which arose on the non-selection plates consisted of both wild type and mutant phenotypes. These results were expected; depending on where replacement-plasmid resolution occur either wild-type or mutant colonies were generated. The initial test to identify double crossover mutants (i.e. nanPU mutants) involved replica-plating colonies onto dextrose starch agar plates with and without antibiotic followed by overnight incubation at 38° C. Kanamycin sensitive colonies were further analyzed by PCR using the nanPU primers described previously. The PCR products of the putative nanPU mutants were compared to those of the wild-type parent using agarose gel electrophoresis. PCR products that were of the expected size were sequenced using the nanPUF (5'-TTC CCT AGC TCA CAG TTA GGT GAT-3') (SEQ ID NO:6) and nanPUR (5'-TCT GCA ATT TCT TTC CAT TCT TTT GGA TCT-3') (SEQ ID NO:16) primers. Also the putative nanPU mutants were sequenced, analyzed by PCR for the absence of temperature sensitive plasmid origin of replication of pCT109GA189 and for the absence of the Tn903 kanamycin resistance element. The nanPU mutants were assayed for uptake of sialic acid from the culture media using the thiobarbituric acid assay 5. A flow diagram showing the construction of P. multocida 1062 nanPU mutant is shown in FIG. 3 (Steps A-F).

A blood agar plate culture of the mutant P. multocida 1062 (serotype A:3) nanPU mutant was obtained from NADC, Ames Iowa on 4 May 2012. The lyophilized powder was rehydrated using sterile distilled water and streaked on TSA plates supplemented with 5% sheep blood and incubated at 37° C. overnight. The next day, three individual colonies were picked and colony PCR was performed using nanPUF 5'-TTC CCT AGC TCA CAG TTA GGT GAT-3' (SEQ ID NO:6) and nanPUR 5'-TCT GCA ATT TCT TTC CAT TCT TTT GGA TCT-3' (SEQ ID NO:16) primers as described earlier (Lawrence et al., 2010). The clones as expected, amplified a band at 1.3 kb, when compared to the parent strain (3.150 kb), indicating a truncated nanPU gene. A single colony from one of the clones was inoculated into autoclaved brain heart infusion (BHI) medium and incubated at 37° C./200 rpm overnight. The next day, cultures were diluted to 0.4 OD (optical density at 600 nm) in BHI broth and allowed to grow until log phase. Once the cultures reached log phase (OD600=0.8), an equal volume of 50% sterile glycerol was added, mixed and aliquoted into 2 ml cryovials (frozen at $6.9\times10^8$ CFU/ml).

The master seed stock was seeded onto TSA plates supplemented with 5% sheep blood, and a single colony was picked to confirm the presence of truncated nanPU by PCR (FIG. 4). The master seed was sent to internal quality control (QC) laboratory for sterility testing according to 9CFR 113.27(b), and was devoid of any extraneous (fungal) growth. The master seed was tested for safety in outbred mice [Hsd:ICR (CD-1®), Harlan], per 9CFR 113.33 and was found to have adverse effect.

The master seed stock was seeded onto TSA plates supplemented with 5% sheep blood, and a single colony was picked and colony PCR was performed as described earlier using nanPUF and nanPUR primers. FIG. 4 shows the image of an agarose gel: 1—MW marker; 2—PCR product of *P. multocida* 1062 P. mult. 1062 Nan showing truncated nanPU gene (1.3 Kb); 3—PCR product of *P. multocida* 1062 wild type showing full length nanPU gene (3.150 Kb); negative control lacking template DNA.

Example 3

Development of *P. multocida* nanPU/hyaD Double Knockout Mutant

To develop a double knockout mutant of *P. multocida* 1062 A:3, a single deletion mutant in hyaD was constructed as described in section IIa and was used as a base to knock out nanPU locus as described in section IIb.

A blood agar plate of mutant *P. multocida* 1062 (serotype A:3) nanPU/hyaD was obtained from NADC, Ames Iowa on 4 May 2012. The lyophilized powder was rehydrated using sterile distilled water and streaked on TSA plates supplemented with 5% sheep blood and incubated at 37° C. overnight. The next day, three individual colonies were picked and colony PCR was performed using nanPUF 5'-TTC CCT AGC TCA CAG TTA GGT GAT-3' (SEQ ID NO:6)/nanPUR 5'-TCT GCA ATT TCT TTC CAT TCT TTT GGA TCT-3' (SEQ ID NO:16) and hyaDF 5'-ATG ATA TTT GAG AAG TCG GCG G-3' (SEQ ID NO:14)/hyaDR 5'-GTA ATT TTC GTT CCC AAG GC-3' (SEQ ID NO:17) primers, as described earlier (Lawrence et al., 2010). The clones as expected, amplified a band at 1.3 kb, when compared to the parent strain (3.150 kb), indicating a truncated nanPU gene. A single colony from one of the clones was inoculated into autoclaved brain heart infusion (BHI) medium and incubated at 37° C./200 rpm overnight. The next day, cultures were diluted to 0.4 OD (optical density at 600 nm) in BHI broth and allowed to grow until log phase. Once the cultures reached log phase (OD600=0.8), an equal volume of 50% sterile glycerol was added, mixed and aliquoted into 2 ml cryovials. The master seed was frozen at a concentration of $2.64\times10^8$ CFU/ml.

The master seed stock was seeded onto TSA plates supplemented with 5% sheep blood, and a single colony was picked to confirm the presence of truncated nanPU and hyaD by PCR (FIG. 5). The master seed was sent to internal quality control (QC) laboratory for sterility testing according to 9CFR 113.27(b), and was devoid of any extraneous (fungal/bacterial) growth. A TSA plate containing P. mult 1062 Nan-Hya-May 8, 2012 was obtained from the QC laboratory and sent to internal diagnostics laboratory for identification/confirmation according to 9CFR 113.64(c)4. After confirming that the growth obtained from the QC laboratory was mutant P. mult 1062 Nan-Hya-May 9, 2012, we analyzed a single colony from the TSA plate again for the presence of truncated nanPU and hyaD gene by PCR. The master seed was tested for safety in outbred mice [Hsd:ICR (CD-1®), Harlan], per 9CFR 113.33 and was found to have no adverse effect.

III. Evaluate the Efficacy of *Pasteurella multocida* Vaccine Candidates Objective:
1. Vaccinate calves with modified live *P. multocida* vaccine through subcutaneous route.
2. Challenge with *P. multocida* 1062 wild type to determine vaccine efficacy.

Materials and Methods:
Product: Log phase cultures of *P. multocida* hyaD, *P. multocida* hyaD/nanPU and *P. multocida* nanPU mutants.
Animals and Housing: There were a total of 15 calves, 4 weeks of age and housed in 4 different pens as described in Table 1.

TABLE 1

Treatment Groups

| Group | Treatment | Total Dose/CFU per animal | Route/volume | Calf Id #. |
|---|---|---|---|---|
| 1 | *P. multocida* hyaD | $1.14 \times 10^9$ | subcutaneous 2 ml | 115, 114, 117 |
| 2 | *P. multocida* hyaD/nanPU | $1.02 \times 10^9$ | subcutaneous 2 ml | 99, 88, 112 |
| 3 | *P. multocida* nanPU | $1.226 \times 10^9$ | subcutaneous 2 ml | 110, 105, 91 |
| 4 | Control | RPMI medium | subcutaneous 2 ml | 119, 89, 97, 95, 94, 101 |

Vaccination:
1. A fresh glycerol stock of *P. multocida* vaccine was grown overnight in BHI medium, plated (TSA) the next day and incubated at 37° C. The following day plates were scraped and diluted into RPMI medium supplemented with 2% inactivated fetal bovine serum. The inoculum was grown at 37° C./200 rpm until desired $OD_{600}$ was achieved.
2. The culture was diluted to $10^9$ CFU/vaccine dose and dilution plated to enumerate the exact CFU/ml the following day.
3. The vaccine was transported on ice and kept on ice during vaccination.
4. Route and dose: subcutaneous, 1 ml per each side of neck.
5. The injection site was observed for adverse reaction.
6. The calves in the control group received RPMI medium only.

The study schedule is described in Table 2.

Challenge: *P. multocida* 1062 Wild Type
1. A fresh glycerol stock of *P. multocida* 1062 was grown O/N in BHI medium, plated (TSA) the next day and incubated at 37° C. The following day plates were scraped and diluted into RPMI medium supplemented with 2% inactivated fetal bovine serum. The inoculum was grown at 37° C./200 rpm until desired $OD_{600}$ was achieved.
2. The culture was diluted to approximately $10^{10}$ CFU/challenge dose and dilution plated to enumerate the exact CFU/ml the following day.
3. The inoculum was transported on ice and kept on ice during challenge.
4. Route: Trans-tracheal using 14G×1 inch needle.
5. Dose: $3.78 \times 10^{10}$ CFU/animal in 20 ml RPMI, chased with 60 ml RPMI.

Once completed the remaining inoculum was immediately dilution plated in the lab.

The calves were monitored for change in behavior including lethargy, coughing, nasal discharge and scored as shown in Table 2. Rectal temperatures were monitored for calves showing clinical signs.

Necropsy Directions:
1. Animals that are dead, weak or showing clinical signs of pneumonia were euthanized and necropsied immediately by a licensed veterinarian.
2. The remaining calves were euthanized humanely on day 5 by injecting pentobarbital (Euthasol, 20-30 ml at the discretion of the assigned veterinarian) per animal.
3. The lungs were scored for pneumonic lesions and recorded as percent lesion on each lobe.
4. The lung tissues were collected for histopathology.
5. Swabs were taken from lungs (lesions) and trachea for the recovery of challenge organism.

TABLE 2

Study Schedule

| Age | Event |
|---|---|
| 4 weeks old | Day 0—bleed, swab and vaccinate |
| | 7 days post vaccination bleed and swab |
| | 18 days post vaccinate—bleed and swab & challenge with *P. multocida* 1062 wild type |
| | Observe clinical signs starting the day of challenge, euthanize any calves if necessary. |
| | Euthanize and necropsy all on day 4 post challenge |

*The calves were observed for feed intake and rectal temperatures taken morning and evening post challenge.

TABLE 3

Clinical signs for scoring
Criteria for Post Challenge Observations

| | |
|---|---|
| 0 = | Normal |
| 1 = | Depression, Anorexia, Cough, Nasal Discharge, Dyspnea |
| 2 = | Severely Depressed, Unable to Rise or Walk, Euthanized for Humane Reasons |
| 3 = | Dead On Arrival (DOA) |

Results:
None of the vaccinated calves showed any injection site swelling, granuloma or anaphylaxis. One day post challenge calf#97 died. The remaining calves in the control group were depressed lethargic and anorexic. The vaccinates and control calves were euthanized on day 4, post challenge. The lungs from the control calves showed severe purulent bronchopneumonia with mild dysplasia of terminal bronchiole epithelium. The control group had an average lung lesion score of 43.26%. The vaccinates on the other hand showed no febrile response. Upon necropsy the lungs from vaccinates showed mild purulent lesions, moderate endobronchial polyps and prior viral infection. Overall all the three vaccine candidates tested significantly reduced the lung lesion when compared to non-vaccinates and can be used as vaccine when injected subcutaneously. However, among the three vaccine candidates tested *P. multocida* nanPU was more potent in reducing the lung lesion (average lung lesion score 10.2%) compared to *P. multocida* hyaD, (average lung lesion score 17.735%) or *P. multocida* hyaD/nanPU (average lung lesion score 13.97%).

\* \* \*

Having thus described in detail preferred embodiments of the present invention, it is to be understood that the inven-

What is claimed is:

1. A method of vaccinating an animal comprising administering a vaccine composition comprising an attenuated *Pasteurella multocida* (*P. multocida*) strain that provides a protective immune response in a bovine against *P. multocida*, or diseases caused by *P. multocida*;
   wherein the attenuated strain comprises deletions or partial deletions in its hyaD gene and its nanPU gene, relative to the virulent parental strain from which the attenuated strain was produced; and
   wherein the nanPU gene present in the attenuated *P. multocida* strain encodes a polypeptide having the sequence set forth in SEQ ID NO:13.

2. The method of claim 1, wherein the bovine is from about 4 weeks old to 6 weeks old.

3. The method of claim 1, wherein the parental strain hyaD gene comprises the sequence set forth in SEQ ID NO: 1 and the parental strain nanPU gene comprises the sequence as set forth in SEQ ID NO: 5.

4. The method of claim 3, wherein the parental strain hyaD gene consists of the sequence set forth in SEQ ID NO: 1 and the parental strain nanPU gene consists of the sequence as set forth in SEQ ID NO: 5.

5. The method of claim 1, wherein the parental strain hyaD gene encodes a protein having the sequence set forth in SEQ ID NO: 2 and the parental strain nanPU gene encodes proteins having the sequences as set forth in SEQ ID NOs:10 and 11.

6. The method of claim 1, wherein the attenuated strain expresses level(s) of HyaD and/or NanP, NanU peptide(s) that are significantly reduced or undetectable, relative to the attenuated strain's corresponding virulent parental strain.

7. The method of claim 1, wherein the attenuated strain has mutations in the same genes, relative to its corresponding virulent parental strain, as does the attenuated strain deposited at the ATCC under the Patent Deposit Designation PTA-120624.

8. The method of claim 1, wherein the attenuated strain is the strain deposited at the ATCC under the Patent Deposit Designation PTA-120624.

9. The method of claim 1, wherein the attenuated strain has a deletion in its hyaD gene such that the attenuated strain produces a truncated protein having the sequence as set forth in SEQ ID NO: 4.

10. The method of claim 1, wherein the attenuated strain has deletions in both its hyaD and nanPU genes, such that the attenuated strain does not produce wild type HyaD, NanP and NanU proteins, as does its corresponding parental strain, but instead produces truncated proteins having the sequences as set forth in SEQ ID NOs: 4 and 13.

11. The method of claim 1, wherein the vaccine composition further comprises a pharmaceutically or veterinary acceptable vehicle, diluent or excipient, and an adjuvant.

12. The method of claim 11, wherein the adjuvant is inactivated bacteria, inactivated virus, fractions of inactivated bacteria, bacterial lipopolysaccharides, bacterial toxins, or combinations thereof.

13. The method of claim 1, wherein the composition further comprises an additional antigen(s) associated with a bovine pathogen other than *P. multocida*.

14. The method of claim 13, wherein the additional antigen(s) elicits in a bovine an immune response against bovine respiratory disease (BRD).

* * * * *

SEQUENCE LISTING

<160> NUMBER OF SEQ ID NOS: 17

<210> SEQ ID NO 1
<211> LENGTH: 2919
<212> TYPE: DNA
<213> ORGANISM: Artificial Sequence
<220> FEATURE:
<223> OTHER INFORMATION: Pm 1062 hyaD nucleotide sequence

<400> SEQUENCE: 1

```
atgaatacat tatcacaagc aataaaagca tataacagca atgactatca attagcactc      60
aaattatttg aaaagtcggc ggaaatctat ggacggaaaa ttgttgaatt tcaaattacc     120
aaatgcaaag aaaaactctc agcacatcct tctgttaatt cagcacatct ttctgtaaat     180
aaagaagaaa aagtcaatgt ttgcgatagt ccgttagata ttgcaacaca actgttactt     240
tccaacgtaa aaaaattagt actttctgac tcggaaaaaa acacgttaaa aaataaatgg     300
aaattgctca ctgagaagaa atctgaaaat gcggaggtaa gagcggtcgc ccttgtacca     360
aaagattttc ccaaagatct ggttttagcg cctttacctg atcatgttaa tgattttaca     420
tggtacaaaa agcgaaagaa aagacttggc ataaaacctg aacatcaaca tgttggtctt     480
tctattatcg ttacaacatt caatcgacca gcaattttat cgattacatt agcctgttta     540
gtaaaccaaa aaacacatta cccgtttgaa gttatcgtga cagatgatgg tagtcaggaa     600
gatctatcac cgatcattcg ccaatatgaa aataaattgg atattcgcta cgtcagacaa     660
aaagataacg gttttcaagc cagtgccgct cggaatatgg gattacgctt agcaaaatat     720
gactttattg gcttactcga ctgtgatatg gcgccaaatc cattatgggt tcattcttat     780
gttgcagagc tattagaaga tgatgattta acaatcattg gtccaagaaa atacatcgat     840
acacaacata ttgacccaaa agacttctta aataacgcga gtttgcttga atcattacca     900
gaagtgaaaa ccaataatag tgttgccgca aaaggggaag aacagtttc tctggattgg     960 cgcttagaac aattcgaaaa aacagaaaat ctccgcttat ccgattcgcc tttccgtttt    1020
tttgcggcgg gtaatgttgc tttcgctaaa aaatggctaa ataaatccgg tttctttgat    1080
gaggaattta tcactgggg tggagaagat gtggaattg gatatcgctt attccgttac     1140
ggtagtttct ttaaaactat tgatggcatt atggcctacc atcaagagcc accaggtaaa    1200 gaaatgaaa ccgatcgtga agcgggaaaa aatattacgc tcgatattat gagagaaaag    1260
gtcccttata tctatagaaa acttttacca atagaagatt cgcatatcaa tagagtacct    1320
ttagtttcaa tttatatccc agcttataac tgtgcaaact atattcaacg ttgcgtagat    1380
agtgcactga atcagactgt tgttgatctc gaggtttgta tttgtaacga tggttcaaca    1440
gataatacct tagaagtgat caataagctt tatggtaata tcctagggt acgcatcatg    1500 tctaaaccaa atggcggaat agcctcagca tcaaatgcag ccgtttcttt tgctaaaggt    1560
tattacattg ggcagttaga ttcagatgat tatcttgagc ctgatgcagt tgaactgtgt    1620
ttaaaagaat ttttaaaaga taaaacgcta gcttgtgttt ataccactaa tagaaacgtc    1680
aatccggatg tagcttaat cgctaatggt tacaattggc cagaattttc acgagaaaaa    1740
ctcacaacgg ctatgattgc tcaccacttt agaatgttca cgattagagc ttggcattta    1800
actgatggat tcaatgaaaa aattgaaaat gccgtagact atgacatgtt cctcaaactc    1860
agtgaagttg gaaaatttaa acatcttaat aaaatctgct ataaccgtgt attacatggt    1920
```

-continued

| | | | | |
|---|---|---|---|---|
| gataacacat | caattaagaa | acttggcatt | caaaagaaaa | accattttgt | tgtagtcaat | 1980 |
| cagtcattaa | atagacaagg | cataacttat | tataattatg | acgaatttga | tgatttagat | 2040 |
| gaaagtagaa | agtatatttt | caataaaacc | gctgaatatc | aagaagagat | tgatatctta | 2100 |
| aaagatatta | aaatcatcca | gaataaagat | gccaaaatcg | cagtcagtat | tttttatccc | 2160 |
| aatacattaa | acggcttagt | gaaaaaacta | aacaatatta | ttgaatataa | taaaaatata | 2220 |
| ttcgttattg | ttctacatgt | tgataagaat | catcttacac | cagatatcaa | aaagaaata | 2280 |
| ctagccttct | atcataaaca | tcaagtgaat | attttactaa | ataatgatat | ctcatattac | 2340 |
| acgagtaata | gattaataaa | aactgaggcg | catttaagta | atattaataa | attaagtcag | 2400 |
| ttaaatctaa | attgtgaata | catcattttt | gataatcatg | acagcctatt | cgttaaaaat | 2460 |
| gacagctatg | cttatatgaa | aaaatatgat | gtcggcatga | atttctcagc | attaacacat | 2520 |
| gattggatcg | agaaaatcaa | tgcgcatcca | ccatttaaaa | agctcattaa | aacttatttt | 2580 |
| aatgacaatg | acttaaaaag | tatgaatgtg | aaagggcat | cacaaggtat | gtttatgacg | 2640 |
| tatgcgctag | cgcatgagct | tctgacgatt | attaaagaag | tcatcacatc | ttgccagtca | 2700 |
| attgatagtg | tgccagaata | taacactgag | gatatttggt | tccaatttgc | acttttaatc | 2760 |
| ttagaaaaga | aaaccggcca | tgtatttaat | aaaacatcga | ccctgactta | tatgccttgg | 2820 |
| gaacgaaaat | tacaatggac | aaatgaacaa | attgaaagtg | caaaagagg | agaaaatata | 2880 |
| cctgttaaca | agttcattat | taatagtata | actctataa | | | 2919 |

<210> SEQ ID NO 2
<211> LENGTH: 972
<212> TYPE: PRT
<213> ORGANISM: Artificial Sequence
<220> FEATURE:
<223> OTHER INFORMATION: Pm 1062 hyaD amino acid sequence

<400> SEQUENCE: 2

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

```
Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Ile Ala Ser Ala Ser Asn
            500                 505                 510

Ala Ala Val Ser Phe Ala Lys Gly Tyr Tyr Ile Gly Gln Leu Asp Ser
        515                 520                 525

Asp Asp Tyr Leu Glu Pro Asp Ala Val Glu Leu Cys Leu Lys Glu Phe
    530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His Phe Arg Met
            580                 585                 590

Phe Thr Ile Arg Ala Trp His Leu Thr Asp Gly Phe Asn Glu Lys Ile
        595                 600                 605
```

Glu Asn Ala Val Asp Tyr Asp Met Phe Leu Lys Leu Ser Glu Val Gly
610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
            645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile Lys
690                 695                 700

Ile Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
                725                 730                 735

Asn Lys Asn Ile Phe Val Ile Val Leu His Val Asp Lys Asn His Leu
            740                 745                 750

Thr Pro Asp Ile Lys Lys Glu Ile Leu Ala Phe Tyr His Lys His Gln
        755                 760                 765

Val Asn Ile Leu Leu Asn Asn Asp Ile Ser Tyr Tyr Thr Ser Asn Arg
770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
                805                 810                 815

Phe Val Lys Asn Asp Ser Tyr Ala Tyr Met Lys Lys Tyr Asp Val Gly
            820                 825                 830

Met Asn Phe Ser Ala Leu Thr His Asp Trp Ile Glu Lys Ile Asn Ala
        835                 840                 845

His Pro Pro Phe Lys Lys Leu Ile Lys Thr Tyr Phe Asn Asp Asn Asp
850                 855                 860

Leu Lys Ser Met Asn Val Lys Gly Ala Ser Gln Gly Met Phe Met Thr
865                 870                 875                 880

Tyr Ala Leu Ala His Glu Leu Leu Thr Ile Ile Lys Glu Val Ile Thr
                885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
        915                 920                 925

Phe Asn Lys Thr Ser Thr Leu Thr Tyr Met Pro Trp Glu Arg Lys Leu
930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970

<210> SEQ ID NO 3
<211> LENGTH: 2694
<212> TYPE: DNA
<213> ORGANISM: Artificial Sequence
<220> FEATURE:
<223> OTHER INFORMATION: Pm 1062 (delta)hyaD (BglII fragment deleted)
      nucleotide sequence

<400> SEQUENCE: 3

```
atgaatacat tatcacaagc aataaaagca ataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct atcaccgatc attcgccaat atgaaaataa attggatatt    420
cgctacgtca gacaaaaaga taacggtttt caagccagtg ccgctcggaa tatgggatta    480
cgcttagcaa aatatgactt tattggctta ctcgactgtg atatggcgcc aaatccatta    540
tgggttcatt cttatgttgc agagctatta gaagatgatg atttaacaat cattggtcca    600
agaaaataca tcgatacaca acatattgac ccaaaagact tcttaaataa cgcgagtttg    660
cttgaatcat taccagaagt gaaaaccaat aatagtgttg ccgcaaaagg ggaaggaaca    720
gtttctctgg attggcgctt agaacaattc gaaaaaacag aaaatctccg cttatccgat    780
tcgccttttcc gttttttgc ggcgggtaat gttgcttttcg ctaaaaaatg gctaaataaa    840
tccggtttct ttgatgagga atttaatcac tggggtggag aagatgtgga atttggatat    900
cgcttattcc gttacggtag tttctttaaa actattgatg gcattatggc ctaccatcaa    960
gagccaccag gtaaagaaaa tgaaaccgat cgtgaagcgg aaaaaatat tacgctcgat    1020
attatgagag aaaaggtccc ttatatctat agaaaacttt taccaataga agattcgcat   1080
atcaatagag tacctttagt ttcaatttat atcccagctt ataactgtgc aaactatatt   1140
caacgttgcg tagatagtgc actgaatcag actgttgttg atctcgaggt ttgtatttgt   1200
aacgatggtt caacagataa taccttagaa gtgatcaata agctttatgg taataatcct   1260
agggtacgca tcatgtctaa accaaatggc ggaatagcct cagcatcaaa tgcagccgtt   1320
tcttttgcta aaggttatta cattgggcag ttagattcag atgattatct tgagcctgat   1380
gcagttgaac tgtgtttaaa agaatttta aaagataaaa cgctagcttg tgtttatacc   1440
actaatagaa acgtcaatcc ggatggtagc ttaatcgcta atggttacaa ttggccagaa   1500
ttttcacgag aaaaactcac aacggctatg attgctcacc actttagaat gttcacgatt   1560
agagcttggc atttaactga tggattcaat gaaaaaattg aaaatgccgt agactatgac   1620
atgttcctca aactcagtga agttggaaaa tttaaacatc ttaataaaat ctgctataac   1680
cgtgtattac atggtgataa cacatcaatt aagaaacttg gcattcaaaa gaaaaaccat   1740
tttgttgtag tcaatcagtc attaaataga caaggcataa cttattataa ttatgacgaa   1800
tttgatgatt tagatgaaag tagaaagtat attttcaata aaaccgctga atatcaagaa   1860
gagattgata tcttaaaaga tattaaaatc atccagaata aagatgccaa aatcgcagtc   1920
agtattttt atcccaatac attaaacggc ttagtgaaaa aactaaacaa tattattgaa   1980
tataataaaa atatattcgt tattgttcta catgttgata agaatcatct tacaccagat   2040
atcaaaaaag aaatactagc cttctatcat aaacatcaag tgaatatttt actaaataat   2100
gatatctcat attacacgag taatagatta ataaaaactg aggcgcattt aagtaatatt   2160
aataaaattaa gtcagttaaa tctaaattgt gaatacatca tttttgataa tcatgacagc   2220
ctattcgtta aaaatgacag ctatgcttat atgaaaaaat atgatgtcgg catgaatttc   2280
tcagcattaa cacatgattg gatcgagaaa atcaatgcgc atccaccatt taaaaagctc   2340
```

```
attaaaactt attttaatga caatgactta aaaagtatga atgtgaaagg ggcatcacaa    2400
ggtatgttta tgacgtatgc gctagcgcat gagcttctga cgattattaa agaagtcatc    2460
acatcttgcc agtcaattga tagtgtgcca gaatataaca ctgaggatat ttggttccaa    2520
tttgcacttt taatcttaga aaagaaaacc ggccatgtat ttaataaaac atcgaccctg    2580
acttatatgc cttgggaacg aaaattacaa tggacaaatg aacaaattga aagtgcaaaa    2640
agaggagaaa atatacctgt taacaagttc attattaata gtataactct ataa          2694
```

<210> SEQ ID NO 4
<211> LENGTH: 897
<212> TYPE: PRT
<213> ORGANISM: Artificial Sequence
<220> FEATURE:
<223> OTHER INFORMATION: Pm 1062 (delta)hyaD (BglII fragment deleted)
      amino acid sequence

<400> SEQUENCE: 4

```
Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Ser
        115                 120                 125

Pro Ile Ile Arg Gln Tyr Glu Asn Lys Leu Asp Ile Arg Tyr Val Arg
    130                 135                 140

Gln Lys Asp Asn Gly Phe Gln Ala Ser Ala Ala Arg Asn Met Gly Leu
145                 150                 155                 160

Arg Leu Ala Lys Tyr Asp Phe Ile Gly Leu Leu Asp Cys Asp Met Ala
                165                 170                 175

Pro Asn Pro Leu Trp Val His Ser Tyr Val Ala Glu Leu Leu Glu Asp
            180                 185                 190

Asp Asp Leu Thr Ile Ile Gly Pro Arg Lys Tyr Ile Asp Thr Gln His
        195                 200                 205

Ile Asp Pro Lys Asp Phe Leu Asn Asn Ala Ser Leu Leu Glu Ser Leu
    210                 215                 220

Pro Glu Val Lys Thr Asn Asn Ser Val Ala Ala Lys Gly Glu Gly Thr
225                 230                 235                 240

Val Ser Leu Asp Trp Arg Leu Glu Gln Phe Glu Lys Thr Glu Asn Leu
                245                 250                 255

Arg Leu Ser Asp Ser Pro Phe Arg Phe Phe Ala Ala Gly Asn Val Ala
            260                 265                 270

Phe Ala Lys Lys Trp Leu Asn Lys Ser Gly Phe Phe Asp Glu Glu Phe
        275                 280                 285

Asn His Trp Gly Gly Glu Asp Val Glu Phe Gly Tyr Arg Leu Phe Arg
    290                 295                 300
```

-continued

| | | | | | | | | | | | |
|---|---|---|---|---|---|---|---|---|---|---|---|
|Tyr|Gly|Ser|Phe|Phe|Lys|Thr|Ile|Asp|Gly|Ile|Met|Ala|Tyr|His|Gln|
|305| | | | |310| | | | |315| | | | |320|

Tyr Gly Ser Phe Phe Lys Thr Ile Asp Gly Ile Met Ala Tyr His Gln
305                 310                 315                 320

Glu Pro Pro Gly Lys Glu Asn Glu Thr Asp Arg Glu Ala Gly Lys Asn
                325                 330                 335

Ile Thr Leu Asp Ile Met Arg Glu Lys Val Pro Tyr Ile Tyr Arg Lys
            340                 345                 350

Leu Leu Pro Ile Glu Asp Ser His Ile Asn Arg Val Pro Leu Val Ser
            355                 360                 365

Ile Tyr Ile Pro Ala Tyr Asn Cys Ala Asn Tyr Ile Gln Arg Cys Val
370                 375                 380

Asp Ser Ala Leu Asn Gln Thr Val Val Asp Leu Glu Val Cys Ile Cys
385                 390                 395                 400

Asn Asp Gly Ser Thr Asp Asn Thr Leu Glu Val Ile Asn Lys Leu Tyr
            405                 410                 415

Gly Asn Asn Pro Arg Val Arg Ile Met Ser Lys Pro Asn Gly Gly Ile
            420                 425                 430

Ala Ser Ala Ser Asn Ala Ala Val Ser Phe Ala Lys Gly Tyr Tyr Ile
            435                 440                 445

Gly Gln Leu Asp Ser Asp Tyr Leu Glu Pro Asp Ala Val Glu Leu
450                 455                 460

Cys Leu Lys Glu Phe Leu Lys Asp Lys Thr Leu Ala Cys Val Tyr Thr
465                 470                 475                 480

Thr Asn Arg Asn Val Asn Pro Asp Gly Ser Leu Ile Ala Asn Gly Tyr
            485                 490                 495

Asn Trp Pro Glu Phe Ser Arg Glu Lys Leu Thr Thr Ala Met Ile Ala
            500                 505                 510

His His Phe Arg Met Phe Thr Ile Arg Ala Trp His Leu Thr Asp Gly
            515                 520                 525

Phe Asn Glu Lys Ile Glu Asn Ala Val Asp Tyr Asp Met Phe Leu Lys
530                 535                 540

Leu Ser Glu Val Gly Lys Phe Lys His Leu Asn Lys Ile Cys Tyr Asn
545                 550                 555                 560

Arg Val Leu His Gly Asp Asn Thr Ser Ile Lys Lys Leu Gly Ile Gln
            565                 570                 575

Lys Lys Asn His Phe Val Val Asn Gln Ser Leu Asn Arg Gln Gly
            580                 585                 590

Ile Thr Tyr Tyr Asn Tyr Asp Glu Phe Asp Asp Leu Asp Glu Ser Arg
            595                 600                 605

Lys Tyr Ile Phe Asn Lys Thr Ala Glu Tyr Gln Glu Glu Ile Asp Ile
            610                 615                 620

Leu Lys Asp Ile Lys Ile Ile Gln Asn Lys Asp Ala Lys Ile Ala Val
625                 630                 635                 640

Ser Ile Phe Tyr Pro Asn Thr Leu Asn Gly Leu Val Lys Lys Leu Asn
            645                 650                 655

Asn Ile Ile Glu Tyr Asn Lys Asn Ile Phe Val Ile Val Leu His Val
            660                 665                 670

Asp Lys Asn His Leu Thr Pro Asp Ile Lys Lys Glu Ile Leu Ala Phe
            675                 680                 685

Tyr His Lys His Gln Val Asn Ile Leu Leu Asn Asn Asp Ile Ser Tyr
            690                 695                 700

Tyr Thr Ser Asn Arg Leu Ile Lys Thr Glu Ala His Leu Ser Asn Ile
705                 710                 715                 720

```
Asn Lys Leu Ser Gln Leu Asn Leu Asn Cys Glu Tyr Ile Ile Phe Asp
            725                 730                 735
Asn His Asp Ser Leu Phe Val Lys Asn Asp Ser Tyr Ala Tyr Met Lys
        740                 745                 750
Lys Tyr Asp Val Gly Met Asn Phe Ser Ala Leu Thr His Asp Trp Ile
    755                 760                 765
Glu Lys Ile Asn Ala His Pro Pro Phe Lys Lys Leu Ile Lys Thr Tyr
770                 775                 780
Phe Asn Asp Asn Asp Leu Lys Ser Met Asn Val Lys Gly Ala Ser Gln
785                 790                 795                 800
Gly Met Phe Met Thr Tyr Ala Leu Ala His Glu Leu Leu Thr Ile Ile
                805                 810                 815
Lys Glu Val Ile Thr Ser Cys Gln Ser Ile Asp Ser Val Pro Glu Tyr
            820                 825                 830
Asn Thr Glu Asp Ile Trp Phe Gln Phe Ala Leu Leu Ile Leu Glu Lys
        835                 840                 845
Lys Thr Gly His Val Phe Asn Lys Thr Ser Thr Leu Thr Tyr Met Pro
    850                 855                 860
Trp Glu Arg Lys Leu Gln Trp Thr Asn Glu Gln Ile Glu Ser Ala Lys
865                 870                 875                 880
Arg Gly Glu Asn Ile Pro Val Asn Lys Phe Ile Ile Asn Ser Ile Thr
                885                 890                 895
Leu
```

<210> SEQ ID NO 5
<211> LENGTH: 4000
<212> TYPE: DNA
<213> ORGANISM: Artificial Sequence
<220> FEATURE:
<223> OTHER INFORMATION: Wild-type 1062 nanPU nucleotide sequence (prior
      to deletion)

<400> SEQUENCE: 5

```
gtaatcccaa cgtaaccaat agaggagaac tcataatgaa atttaaaaaa ctactacttg      60
catctttatg tttaggtgtt tcagcttctg tatttgcagc agattacgat cttaaattcg     120
gtatggttgc gggtccaagc tcaaacgaat ataaagcagt agaattcttt gcgaaagaag     180
tgaaagaaaa atccaatggc aaaattgatg tggctatttt ccctagctca cagttaggtg     240
atgaccgtgt gatgattaaa caattaaaag acggtgcatt agactttacg ttaggtgaat     300
cagcacgttt ccaaatttac ttcccagaag cagaagtatt tgcgttgcct tatatgattc     360
ctaattttga aacctctaaa aaagcgttgc tcgacacaaa atttggtcaa ggtttattga     420
aaaaaattga taagagttta aacgtacaag tgttatctgt ggcgtataac ggtacacgtc     480
aaacaacttc taaccgtgca atcaacagca ttgaagacat gaaagggtta aaattacgtg     540
tacctaacgc ggcaaccaac cttgcttatg caaaatacgt gggtgcagcg ccaacaccaa     600
tggcattctc tgaagtttac cttgcgcttc aaacaaactc tgtggatggt caagaaaacc     660
cattaccgac aatccaagca caaaaattct atgaagtaca aaatacttta gcgttaacta     720
accacatctt aaatgaccaa ctttacttaa tcagtaacga tacgttggca gatttaccag     780
aagatttaca aaaagtggtt aaagatgcag cagcgaaagc cgctgaatat cacactaaac     840
tcttcgttga cggtgagaac agcttagttg aattcttcaa aagtcaaggt gtgacagtca     900
cacaaccaga cttaaaacca tttaaagcag cacttacacc atactatgat gaatatctca     960
agaaaaatgg tgaagtcggt aaaatggcga ttgaagaaat ttctaatctc gctaaataaa    1020
```

```
tatagtaacc ttatccctgc gccttaaggg ataaggttcc tttttattgg gttgtcttga    1080
ggtatctatg aaaataataa ataaattaga agagtggatt ggcggtgtgc tattcattgg    1140
aattttctta attctgttag cacaaatcat tgctcgtcaa gtgtttcagt caccgtttat    1200
ttggagtgaa gaactcgcaa gattgctatt tatctatgtc gggctacttg gtatcagcat    1260
gggtatccgt agtcagcagc atgtttatat tgatttttta actaacttta tgcccgagaa    1320
agtgagaaag gtgacaaact cctttgttca agttctcatc tttatttcca tcattatttt    1380
cattcattta ggctttaaag tttggatcga ctccagtttt aaaatggaag cgttaactgc    1440
tttcgcttca gatttaattg ggcgcgagac gattgtgcct gaaaaatgga tgtatgcggc    1500
attgcctttt atttcttgtt taatgttatt ccgcttttc caagcgcaag ttgaaaatta    1560
tagaaataag ttaagttata ttcctgtcac ggcatttgtg attggtgcgg tcattatttt    1620
tgcgatttta ttgattgagc cagattggta taaagtcctc cgtatttcaa attatgtgaa    1680
atttggtggt gatgcagtgt atatcacatt agtgatttgg cttgtcatta tgtttgtggg    1740
aaccccggta ggttggtcat tatttattgc gacgttgctt tattttgcga tgacgcgttg    1800
gaatattgtt aactcggcat caaccaagct caccgacagt ttaaatagtt tcccattatt    1860
gagtgtgccg ttctttattt taaccggtat tttaatgaat acgggcggaa ttacagaacg    1920
tattttgat ttcgcacgtg cctttgctcgg tcattaccgt ggtggtatgg gacacgtgaa    1980
tatcggggca gtttaatttt tctcaggtat gtctggttct gcacttgccg atgcaggtgg    2040
tttaggccag ttagaaatta aagccatgcg tgatgctggg tatgacgatg acatctgtgg    2100
tgggattacc gctgcttctt gtattatcgg tccattagtt ccaccaagta ttgcgatgat    2160
tatctatggg gttatttcta accaatctat tgcaaaatta tttattgcgg gttttattcc    2220
tggtgtgctc gtaaccattg cgttaatgat catgaactat tatgtggcga aaaaacgtgg    2280
ttatccaaga acacctaaag cgacccttga acaacgttgt caggcattta aaaaggccat    2340
ttgggcagtg ttaaccccaa ttttgattat cggtggtatt ttctctggtc tctttacacc    2400
aacggaagcc gcggtgattg cagccttcta ttccattatt atcgggatgt tgtttaccg    2460
agagttgaat ttacaaatgt tgttcaaaag ctgtattgaa gcaatggcga ttacaggggg    2520
aacagcatta atggtgatga cggtcacttt ctttggtgac atgattgcac gtgagcaagt    2580
ggctatgaaa attgcagaag tctttgttgc agtagccgat tcaccaacga tggtgttagt    2640
catgatcaac ttattgctct tgttccttgg tatgtttatt gatgctttag cattgcaatt    2700
cttggtgtta ccaatgttaa ttccaattgc ggttcacttt ggcattgact taattttctt    2760
tggtgtcatg accacattaa atatgatgat tggtatttg actccaccaa tgggaatggc    2820
attatttgtt gtggcacgtg ttggtaatat gccagtgagt acagtcgcaa aaggggtttt    2880
accttttctta gtaccaattt ttgtgacact ggtgttgatt acaatttcc cacaaattat    2940
caccttata ccaaatcttc tgatgccata atggcgtgaa gaaatggcat tcaaagccaa    3000
tcggactcgg ttggctttaa tttaaaaaac ttgccattca gaattatgct atctgaatcg    3060
gtattcattc ttactaacct aattaattga ggtaataaaa tgaaatttac aaaaacagcg    3120
ttatttacgg tattagcagc aacggcattt gccgcacaag caggtcagta tccagattta    3180
ccagaaggca ttaaagccgg tgcaggtgca ttaattggtg ataccgttta tgtggggtta    3240
ggtggtactg gcacaacaaa attctattca ttaaatttga agatccaaa agagtggaaa    3300
gaaattgcag aattccctgg tggtaaacgt aatcagcctg ttgctgcggg tgtgaatggt    3360
```

-continued

```
aagctttatg tgtttggtgg tttccaagat acagatgtcg cgaaaaatca aattatcaat    3420
gatgcttatg agtataatcc ggcagataat acgtggacaa aattaagcac acgttctcct    3480
cgttcaacat ctgtgggagc gagtgttgca gcagatggcg gtaaaattta cttcgtaggt    3540
ggggtaaacc acgaaatttg gaatggttta ttccaagatg ttaaagctgc aggtggtgat    3600
aaagagaaag aaaaagcgat ctttgacccg tatttcaatt tacgcgcaca agatttcttc    3660
ttctcaccag aaatcatcag ttatgagcca gctaacaatg tatggcgtaa cgaaggctac    3720
ttcccatatt cgggtcgtgc aggcgctgcg gttgcgatta agatggtaa attattagtc    3780 gtgaatggtg aagtgaaagc aggtttacgc tcgccaggta ctgcgttagg tacgattggt    3840
aaagatggcg ttacttggaa aaaactcggt gatttaccag caccaacagg ctatgacaaa    3900
caagatggta ttgcaggcgg tatgggtggt tataccaatg gtcattatat cgtgacaggt    3960
ggtgcgaact tccctggtgc attagcaaac tatgaaaaag                           4000
```

<210> SEQ ID NO 6
<211> LENGTH: 24
<212> TYPE: DNA
<213> ORGANISM: Artificial Sequence
<220> FEATURE:
<223> OTHER INFORMATION: 1062nanPU_F primer

<400> SEQUENCE: 6

```
ttccctagct cacagttagg tgat                                             24
```

<210> SEQ ID NO 7
<211> LENGTH: 27
<212> TYPE: DNA
<213> ORGANISM: Artificial Sequence
<220> FEATURE:
<223> OTHER INFORMATION: 1062nanPU_delR primer

<400> SEQUENCE: 7

```
gtcacacctt gacttttgaa gaattca                                          27
```

<210> SEQ ID NO 8
<211> LENGTH: 26
<212> TYPE: DNA
<213> ORGANISM: Artificial Sequence
<220> FEATURE:
<223> OTHER INFORMATION: 1062nanPU_delF primer

<400> SEQUENCE: 8

```
aattccaatt gcggttcact ttggca                                           26
```

<210> SEQ ID NO 9
<211> LENGTH: 27
<212> TYPE: DNA
<213> ORGANISM: Artificial Sequence
<220> FEATURE:
<223> OTHER INFORMATION: 1062nanPU_R primer

<400> SEQUENCE: 9

```
tctgcaattt ctttccattc ttttgga                                          27
```

<210> SEQ ID NO 10
<211> LENGTH: 327
<212> TYPE: PRT
<213> ORGANISM: Artificial Sequence
<220> FEATURE:
<223> OTHER INFORMATION: WILD-TYPE NANP AMINO ACID SEQUENCE

<400> SEQUENCE: 10

```
Met Lys Phe Lys Lys Leu Leu Ala Ser Leu Cys Leu Gly Val Ser
1               5                   10                  15

Ala Ser Val Phe Ala Ala Asp Tyr Asp Leu Lys Phe Gly Met Val Ala
            20                  25                  30

Gly Pro Ser Ser Asn Glu Tyr Lys Ala Val Glu Phe Ala Lys Glu
            35                  40                  45

Val Lys Glu Lys Ser Asn Gly Lys Ile Asp Val Ala Ile Phe Pro Ser
50                  55                  60

Ser Gln Leu Gly Asp Asp Arg Val Met Ile Lys Gln Leu Lys Asp Gly
65                  70                  75                  80

Ala Leu Asp Phe Thr Leu Gly Glu Ser Ala Arg Phe Gln Ile Tyr Phe
                85                  90                  95

Pro Glu Ala Glu Val Phe Ala Leu Pro Tyr Met Ile Pro Asn Phe Glu
                100                 105                 110

Thr Ser Lys Lys Ala Leu Leu Asp Thr Lys Phe Gly Gln Gly Leu Leu
                115                 120                 125

Lys Lys Ile Asp Lys Glu Leu Asn Val Gln Val Leu Ser Val Ala Tyr
130                 135                 140

Asn Gly Thr Arg Gln Thr Thr Ser Asn Arg Ala Ile Asn Ser Ile Glu
145                 150                 155                 160

Asp Met Lys Gly Leu Lys Leu Arg Val Pro Asn Ala Ala Thr Asn Leu
                165                 170                 175

Ala Tyr Ala Lys Tyr Val Gly Ala Ala Pro Thr Pro Met Ala Phe Ser
                180                 185                 190

Glu Val Tyr Leu Ala Leu Gln Thr Asn Ser Val Asp Gly Gln Glu Asn
                195                 200                 205

Pro Leu Pro Thr Ile Gln Ala Gln Lys Phe Tyr Glu Val Gln Lys Tyr
210                 215                 220

Leu Ala Leu Thr Asn His Ile Leu Asn Asp Gln Leu Tyr Leu Ile Ser
225                 230                 235                 240

Asn Asp Thr Leu Ala Asp Leu Pro Glu Asp Leu Gln Lys Val Val Lys
                245                 250                 255

Asp Ala Ala Ala Lys Ala Ala Glu Tyr His Thr Lys Leu Phe Val Asp
                260                 265                 270

Gly Glu Asn Ser Leu Val Glu Phe Phe Lys Ser Gln Gly Val Thr Val
                275                 280                 285

Thr Gln Pro Asp Leu Lys Pro Phe Lys Ala Ala Leu Thr Pro Tyr Tyr
                290                 295                 300

Asp Glu Tyr Leu Lys Lys Asn Gly Glu Val Gly Lys Met Ala Ile Glu
305                 310                 315                 320

Glu Ile Ser Asn Leu Ala Lys
                325

<210> SEQ ID NO 11
<211> LENGTH: 627
<212> TYPE: PRT
<213> ORGANISM: Artificial Sequence
<220> FEATURE:
<223> OTHER INFORMATION: WILD-TYPE NANU AMINO ACID SEQUENCE

<400> SEQUENCE: 11

Met Lys Ile Ile Asn Lys Leu Glu Glu Trp Ile Gly Gly Val Leu Phe
1               5                   10                  15

Ile Gly Ile Phe Leu Ile Leu Leu Ala Gln Ile Ile Ala Arg Gln Val
            20                  25                  30
```

```
Phe Gln Ser Pro Phe Ile Trp Ser Glu Glu Leu Ala Arg Leu Leu Phe
        35                  40                  45

Ile Tyr Val Gly Leu Leu Gly Ile Ser Met Gly Ile Arg Ser Gln Gln
 50                  55                  60

His Val Tyr Ile Asp Phe Leu Thr Asn Phe Met Pro Glu Lys Val Arg
 65                  70                  75                  80

Lys Val Thr Asn Ser Phe Val Gln Val Leu Ile Phe Ile Ser Ile Ile
                 85                  90                  95

Ile Phe Ile His Leu Gly Phe Lys Val Trp Ile Asp Ser Ser Phe Lys
                100                 105                 110

Met Glu Ala Leu Thr Ala Phe Ala Ser Asp Leu Ile Gly Arg Glu Thr
                115                 120                 125

Ile Val Pro Glu Lys Trp Met Tyr Ala Ala Leu Pro Phe Ile Ser Cys
        130                 135                 140

Leu Met Leu Phe Arg Phe Phe Gln Ala Gln Val Glu Asn Tyr Arg Asn
145                 150                 155                 160

Lys Leu Ser Tyr Ile Pro Val Thr Ala Phe Val Ile Gly Ala Val Ile
                165                 170                 175

Ile Phe Ala Ile Leu Leu Ile Glu Pro Asp Trp Tyr Lys Val Leu Arg
                180                 185                 190

Ile Ser Asn Tyr Val Lys Phe Gly Gly Asp Ala Val Tyr Ile Thr Leu
                195                 200                 205

Val Ile Trp Leu Val Ile Met Phe Val Gly Thr Pro Val Gly Trp Ser
        210                 215                 220

Leu Phe Ile Ala Thr Leu Leu Tyr Phe Ala Met Thr Arg Trp Asn Ile
225                 230                 235                 240

Val Asn Ser Ala Ser Thr Lys Leu Thr Asp Ser Leu Asn Ser Phe Pro
                245                 250                 255

Leu Leu Ser Val Pro Phe Phe Ile Leu Thr Gly Ile Leu Met Asn Thr
                260                 265                 270

Gly Gly Ile Thr Glu Arg Ile Phe Asp Phe Ala Arg Ala Leu Leu Gly
        275                 280                 285

His Tyr Arg Gly Gly Met Gly His Val Asn Ile Gly Ala Ser Leu Ile
        290                 295                 300

Phe Ser Gly Met Ser Gly Ser Ala Leu Ala Asp Ala Gly Gly Leu Gly
305                 310                 315                 320

Gln Leu Glu Ile Lys Ala Met Arg Asp Ala Gly Tyr Asp Asp Asp Ile
                325                 330                 335

Cys Gly Gly Ile Thr Ala Ala Ser Cys Ile Ile Gly Pro Leu Val Pro
                340                 345                 350

Pro Ser Ile Ala Met Ile Ile Tyr Gly Val Ile Ser Asn Gln Ser Ile
        355                 360                 365

Ala Lys Leu Phe Ile Ala Gly Phe Ile Pro Gly Val Leu Val Thr Ile
        370                 375                 380

Ala Leu Met Ile Met Asn Tyr Tyr Val Ala Lys Arg Gly Tyr Pro
385                 390                 395                 400

Arg Thr Pro Lys Ala Thr Leu Glu Gln Arg Cys Gln Ala Phe Lys Lys
                405                 410                 415

Ala Ile Trp Ala Val Leu Thr Pro Ile Leu Ile Gly Gly Ile Phe
                420                 425                 430

Ser Gly Leu Phe Thr Pro Thr Glu Ala Ala Val Ile Ala Ala Phe Tyr
        435                 440                 445
```

```
Ser Ile Ile Ile Gly Met Phe Val Tyr Arg Glu Leu Asn Leu Gln Met
450                 455                 460

Leu Phe Lys Ser Cys Ile Glu Ala Met Ala Ile Thr Gly Val Thr Ala
465                 470                 475                 480

Leu Met Val Met Thr Val Thr Phe Phe Gly Asp Met Ile Ala Arg Glu
                485                 490                 495

Gln Val Ala Met Lys Ile Ala Glu Val Phe Ala Val Ala Asp Ser
            500                 505                 510

Pro Thr Met Val Leu Val Met Ile Asn Leu Leu Leu Phe Leu Gly
            515                 520                 525

Met Phe Ile Asp Ala Leu Ala Leu Gln Phe Leu Val Leu Pro Met Leu
530                 535                 540

Ile Pro Ile Ala Val His Phe Gly Ile Asp Leu Ile Phe Phe Gly Val
545                 550                 555                 560

Met Thr Thr Leu Asn Met Met Ile Gly Ile Leu Thr Pro Pro Met Gly
                565                 570                 575

Met Ala Leu Phe Val Val Ala Arg Val Gly Asn Met Pro Val Ser Thr
                580                 585                 590

Val Ala Lys Gly Val Leu Pro Phe Leu Val Pro Ile Phe Val Thr Leu
                595                 600                 605

Val Leu Ile Thr Ile Phe Pro Gln Ile Ile Thr Phe Ile Pro Asn Leu
610                 615                 620

Leu Met Pro
625

<210> SEQ ID NO 12
<211> LENGTH: 2146
<212> TYPE: DNA
<213> ORGANISM: Artificial Sequence
<220> FEATURE:
<223> OTHER INFORMATION: mutant 1062 nanpu

<400> SEQUENCE: 12
gtaatcccaa cgtaaccaat agaggagaac tcataatgaa atttaaaaaa ctactacttg      60
catctttatg tttaggtgtt tcagcttctg tatttgcagc agattacgat cttaaattcg     120
gtatggttgc gggtccaagc tcaaacgaat ataaagcagt agaattcttt gcgaaagaag     180
tgaaagaaaa atccaatggc aaaattgatg tggctatttt ccctagctca cagtaggtg      240 atgaccgtgt gatgattaaa caattaaaag acggtgcatt agactttacg ttaggtgaat     300
cagcacgttt ccaaatttac ttcccagaag cagaagtatt tgcgttgcct tatatgattc     360
ctaattttga aacctctaaa aaagcgttgc tcgacacaaa atttggtcaa ggtttattga     420
aaaaaattga taagagttta acgtacaag tgttatctgt ggcgtataac ggtacacgtc      480
aaacaacttc taaccgtgca atcaacagca ttgaagacat gaagggttta aaattacgtg     540
tacctaacgc ggcaaccaac cttgcttatg caaaatacgt gggtgcagcg ccaacaccaa     600
tggcattctc tgaagtttac cttgcgcttc aaacaaactc tgtggatggt caagaaaacc     660
cattaccgac aatccaagca caaaaattct atgaagtaca aaaatactta gcgttaacta     720
accacatctt aaatgaccaa ctttacttaa tcagtaacga tacgttggca gatttaccag     780
aagatttaca aaaagtggtt aaagatgcag cagcgaaagc cgctgaatat cacactaaac     840
tcttcgttga cggtgagaac agcttagttg aattgcggtt cactttggca ttgacttaat     900
tttctttggt gtcatgacca cattaaatat gatgattggt attttgactc caccaatggg     960
aatggcatta tttgttgtgg cacgtgttgg taatatgcca gtgagtacag tcgcaaaagg    1020
```

```
ggttttacct ttcttagtac caattttttgt gacactggtg ttgattacaa ttttcccaca   1080
aattatcacc tttataccaa atcttctgat gccataatgg cgtgaagaaa tggcattcaa   1140
agccaatcgg actcggttgg ctttaattta aaaaacttgc cattcagaat tatgctatct   1200
gaatcggtat tcattcttac taacctaatt aattgaggta ataaaatgaa atttacaaaa   1260
acagcgttat ttacggtatt agcagcaacg gcatttgccg cacaagcagg tcagtatcca   1320
gatttaccag aaggcattaa agccggtgca ggtgcattaa ttggtgatac cgtttatgtg   1380
gggttaggtg gtactggcac aacaaaattc tattcattaa atttgaaaga tccaaaagag   1440
tggaaagaaa ttgcagaatt ccctggtggt aaacgtaatc agcctgttgc tgcgggtgtg   1500
aatggtaagc tttatgtgtt tggtggtttc caagatacag atgtcgcgaa aaatcaaatt   1560
atcaatgatg cttatgagta taatccggca gataatacgt ggacaaaatt aagcacacgt   1620
tctcctcgtt caacatctgt gggagcgagt gttgcagcag atggcggtaa aatttacttc   1680
gtaggtgggg taaccacga aatttggaat ggtttattcc aagatgttaa agctgcaggt   1740
ggtgataaag agaaagaaaa agcgatcttt gacccgtatt tcaatttacg cgcacaagat   1800
ttcttcttct caccagaaat catcagttat gagccagcta acaatgtatg gcgtaacgaa   1860
ggctacttcc catattcggg tcgtgcaggc gctgcggttg cgattaaaga tggtaaatta   1920
ttagtcgtga atggtgaagt gaaagcaggt ttacgctcgc caggtactgc gttaggtacg   1980
attggtaaag atggcgttac ttggaaaaaa ctcggtgatt taccagcacc aacaggctat   2040
gacaaacaag atggtattgc aggcggtatg ggtggttata ccaatggtca ttatatcgtg   2100
acaggtggtg cgaacttccc tggtgcatta gcaaactatg aaaaag                  2146
```

<210> SEQ ID NO 13
<211> LENGTH: 287
<212> TYPE: PRT
<213> ORGANISM: Artificial Sequence
<220> FEATURE:
<223> OTHER INFORMATION: MUTANT NANP AMINO ACID SEQUENCE (DEDUCED)

<400> SEQUENCE: 13

```
Met Lys Phe Lys Lys Leu Leu Leu Ala Ser Leu Cys Leu Gly Val Ser
1               5                   10                  15

Ala Ser Val Phe Ala Ala Asp Tyr Asp Leu Lys Phe Gly Met Val Ala
            20                  25                  30

Gly Pro Ser Ser Asn Glu Tyr Lys Ala Val Glu Phe Ala Lys Glu
        35                  40                  45

Val Lys Glu Lys Ser Asn Gly Lys Ile Asp Val Ala Ile Phe Pro Ser
    50                  55                  60

Ser Gln Leu Gly Asp Asp Arg Val Met Ile Lys Gln Leu Lys Asp Gly
65                  70                  75                  80

Ala Leu Asp Phe Thr Leu Gly Glu Ser Ala Arg Phe Gln Ile Tyr Phe
                85                  90                  95

Pro Glu Ala Glu Val Phe Ala Leu Pro Tyr Met Ile Pro Asn Phe Glu
            100                 105                 110

Thr Ser Lys Lys Ala Leu Leu Asp Thr Lys Phe Gly Gln Gly Leu Leu
        115                 120                 125

Lys Lys Ile Asp Lys Glu Leu Asn Val Gln Val Leu Ser Val Ala Tyr
    130                 135                 140

Asn Gly Thr Arg Gln Thr Thr Ser Asn Arg Ala Ile Asn Ser Ile Glu
145                 150                 155                 160
```

```
Asp Met Lys Gly Leu Lys Leu Arg Val Pro Asn Ala Ala Thr Asn Leu
            165                 170                 175

Ala Tyr Ala Lys Tyr Val Gly Ala Ala Pro Thr Pro Met Ala Phe Ser
        180                 185                 190

Glu Val Tyr Leu Ala Leu Gln Thr Asn Ser Val Asp Gly Gln Glu Asn
    195                 200                 205

Pro Leu Pro Thr Ile Gln Ala Gln Lys Phe Tyr Glu Val Gln Lys Tyr
210                 215                 220

Leu Ala Leu Thr Asn His Ile Leu Asn Asp Gln Leu Tyr Leu Ile Ser
225                 230                 235                 240

Asn Asp Thr Leu Ala Asp Leu Pro Glu Asp Leu Gln Lys Val Val Lys
                245                 250                 255

Asp Ala Ala Lys Ala Ala Glu Tyr His Thr Lys Leu Phe Val Asp
            260                 265                 270

Gly Glu Asn Ser Leu Val Glu Leu Arg Phe Thr Leu Ala Leu Thr
            275                 280                 285
```

<210> SEQ ID NO 14
<211> LENGTH: 22
<212> TYPE: DNA
<213> ORGANISM: Artificial Sequence
<220> FEATURE:
<223> OTHER INFORMATION: p. multocida 1062 hyad forward primer

<400> SEQUENCE: 14
atgatatttg agaagtcggc gg       22

<210> SEQ ID NO 15
<211> LENGTH: 21
<212> TYPE: DNA
<213> ORGANISM: Artificial Sequence
<220> FEATURE:
<223> OTHER INFORMATION: p. multocida 1062 hyad reverse primer

<400> SEQUENCE: 15
tgtaattttc gttcccaagg c       21

<210> SEQ ID NO 16
<211> LENGTH: 30
<212> TYPE: DNA
<213> ORGANISM: Artificial Sequence
<220> FEATURE:
<223> OTHER INFORMATION: nanpur screening/sequencing primer

<400> SEQUENCE: 16
tctgcaattt ctttccattc ttttggatct       30

<210> SEQ ID NO 17
<211> LENGTH: 20
<212> TYPE: DNA
<213> ORGANISM: Artificial Sequence
<220> FEATURE:
<223> OTHER INFORMATION: hyadr screening primer

<400> SEQUENCE: 17
gtaattttcg ttcccaaggc       20